US007071316B1

(12) United States Patent
Masure et al.

(10) Patent No.: US 7,071,316 B1
(45) Date of Patent: Jul. 4, 2006

(54) HUMAN AKT-3

(75) Inventors: Stefan Leo Jozef Masure, Brasschaat (BE); Alan Richardson, Kasterlee (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/869,079

(22) PCT Filed: Dec. 17, 1999

(86) PCT No.: PCT/GB99/04311

§ 371 (c)(1),
(2), (4) Date: Jun. 20, 2001

(87) PCT Pub. No.: WO00/37613

PCT Pub. Date: Jun. 29, 2000

(30) Foreign Application Priority Data

Dec. 22, 1998 (GB) ................................ 9828375.7

(51) Int. Cl.
  *C12N 15/12* (2006.01)
  *C12N 15/54* (2006.01)
  *C12N 15/63* (2006.01)
  *C12N 5/10* (2006.01)
  *C12N 1/11* (2006.01)
(52) U.S. Cl. .................... 536/23.2; 536/23.1; 536/23.5; 435/320.1; 435/325; 435/252.3
(58) Field of Classification Search ................ 435/325, 435/320.1, 7.2; 536/23.1, 23.2, 23.5
See application file for complete search history.

(56) References Cited

OTHER PUBLICATIONS

Ahmed, N.N., et al., "Transduction of interleukin-2 antiapoptotic and proliferative signals via Akt protein kinase," Proc. Natl Acad Sci USA (1997) 94:3627-3632.
Alessi, D.R., et al., "Mechanism of activation and function of protein kinase B." Current Opinion Gen. Dev. (1998) 8:55-62.
Allessi, D.R., et al., "Mechanism of activation of protein kinase B by insulin and IGF-1" EMBO Journal (1996) 15:6541-6551.
Alessi, D.R., et al., "3-phosphoinositide-dependent protein kinase-1 (PDK1): structural and functional homology with the *Drosophila* DSTP61 kinase." Curr. Biol. (1997) 7:776-789.
Altomare, D.A., et. al., "Cloning, chromosomal localization and expression analysis of the mouse Akt2 oncogene." Oncogene (1995) 11:1055-1060
Altschul, S.F., et al., "Basic Local Alignment Search Tool," J. Mol. Biol. (1990) 215:403-410.
Bellacosa, A., et al, "Structure, expression and chromosomal mapping of c-akt: relationship to v-akt and its implications" Oncogene (1993) 8:745-754.

Bellacosa, A., et al., "Molecular Alterations Of The Akt2 Oncogene In Ovarian And Breast Carcinomas," Int. J. Cancer (1995) 64:280-285.
Cheng, J.Q, et al., "AKT2, a putative oncogene encoding a member of a subfamily of protein-serine/threonine kinases, is amplified in human ovarian carcinomas," Proc. Natl. Acad. Sci. USA (1992) 89:9267-9271.
Brodbeck, D., et al., "A Human Protein Kinase By with Regulatory Phosphorylation Sites in the Activation Loop and in the C-terminal Hydrophobic Domain", The Journal of Biological Chemistry 1999 vol. 274:9133-9136.
Chien, C., et al., "The two-hybrid system: A method to identify and clone genes for proteins that interact with a protein of interest," Proc. Natl., Acad., Sci. USA 1991 vol. 88:9578-9582.
Coffer, P.J., et al., "Molecular cloning and characterisation of a novel putative protein-serine kinase related to the cAMP-dependent and protein kinase C families," Eur. J. Biochem. 1991 201:475-481.
Cohen, P., et al., "PDK1, one of the missing links in insulin signal transduction?", FEBS Letters 1997 410:3-10.
Cooney, M., et al., "Site-Specific Oligonucleotide Binding Represses Transcription of the Human c-myc Gene in Vitro," Science 1988 vol. 241:456-459.
Crowder, R.J., et al., "Phosphatidylinositol 3-Kinase and Akt Protein Kinase Are Necessary and Sufficient for the Survival of Nerve Growth Factor-Dependent Sympathetic Neurons," Journal of Neuroscience 1998 vol. 18 (8):2933-2943.
Datta, S.R., et al., "Akt Phosphorylation of BAD Couples Survival Signals to the Cell-Intrinsic Death Machinery," Cell. 1997 vol. 91:231-241.
Davis, P.D., et al., "Inhibitors of Protein Kinase C. 2. Substituted Bisindolylmaleimides with Improved Potency and Selectivity," J. Med. Chem., 1992 vol. 35:994-1001.
del Peso, L., et al., "Interleukin-3-Induced Phosphorylation of BAD Through the Protein Kinase Akt", Science 1997 vol. 278:687-689.
Delcommenne, M., et al., "Phosphoinositide-3-OH kinase-dependent regulation of glycogen synthase kinase 3 and protein kinase B/AKT by the integrin-linked kinase," Proc. Natl. Acad Science USA (1998) vol. 95:11211-11216.

(Continued)

*Primary Examiner*—Scott D. Priebe

(57) ABSTRACT

There is disclosed a nucleic acid molecule encoding human Akt-3 protein or a functional equivalent or bioprecursor thereof comprising the amino acid sequence illustrated in Sequence ID No. 3. The human Akt-3 protein itself also forms part of the invention. The nucleic acid molecule and the human Akt-3 protein may themselves be used as medicaments, or in the preparation of medicaments for treating cancer, in their own right or in the form of a pharmaceutically acceptable carrier, diluent or excipient thereof. Further disclosed are methods of identifying agents which influence the activity of a human Akt-3 protein.

9 Claims, 9 Drawing Sheets

OTHER PUBLICATIONS

Beal, P.A., et al., "Second Structural Motif for Recognition of DNA by Oligonucleotide-Directed Triple-Helix Formation," Science (1991) 251:1360-1363.
Eves, E.M., et al., "Akt, a Target of Phosphatidylinositol 3-Kinase, Inhibits Apoptosis in a Differentiating Neuronal Cell Line," Molecular and Cellular Biology (1998) vol. 18 (4):2143-2152.
Frisch, S.M., et al., "Integrins and anoikis," Current Opinion in Cell Biol (1997) 9:701-706.
Frisch, S.M., et al., "Disruption of Epithelial Cell-Matrix Interactions Induces Apoptosis," Journal of Cell Biology (1994) vol. 124:619-626.
Hanks, S.T.,et al., The eukaryotic protein kinase superfamily: kinase (catalytic) domain structure and classification(1) FASEB Journal (1995) vol. 9:576-596.
Hemming, B.A., "Akt Signaling: Linking Membrane Events to Life and Death Decisions," Science (1997) 275:628-630.
Heng, H.H., et al., "High-resolution mapping of mammalian genes by in situ hybridization to free chromatin," Proc Natl Acad Sci USA (1992) 89:9509-9513.
Heng, H.Q., et al., "Modes of DAPI banding and simultaneous in situ hybridization," Chromosoma (1993) 102:325-332.
Jones, P.F., et al., "Molecular cloning and identification of a serine/threonine protein kinase of the second-messenger subfamily", Proc Natl Acad. Sci, USA (1991) 88:4171-4175.
Kauffmann-Zeh, A., et al., "Suppression of c-Myc-induced apoptosis by Ras signalling through PI(3)K and PKB", Nature (1997) 385:544-548.
Kennedy, S.G., et al., "The PI 3-kinase/Akt signaling pathway delivers an anti-apoptotic signal", Genes & Development 1997 11:701-713.
Khwaja, A., et al., "Matrix adhesion and Ras transformation both activate a phosphoinositide 3-OH kinase and protein kinase B/akt cellular survival pathway," The EMBO Journal (1997) vol. 16 (10) 2783-2793.
Konishi, H., et al., "Molecular Cloning of Rat Rac Protein Kinase α And β and their association with protein kinase Cξ *", Biochemical and Biophysical Research Communications (1994) vol. 205 (1) 817-825.
Konishi, H., et al., "Molecular Cloning and Characterization of a New Member of the RAC Protein Kinase Family: Association of the Pleckstrin Homology Domain of three types of RAC protein kinase with protein Kinase C subspecies and βγ Subunits of G Proteins*," Biochemical and Biophysical Research Communications( 1995) vol. 216 (2) 526-534.
Kulik, G., et al., "Antiapoptotic Signalling by the Insulin-Like Growth Factor I Receptor, Phosphatidylinositol 3-Kinase, and Akt", Molecular and Cellular Biology, (1997) vol. 17 (3) 1595-1606.
Lee, J.S., et al., "Complexes formed by (pyrimidine)n (purine)n DNAS on lowering the pH are three-stranded," Nucleic Acids Research (1979) vol. 6:3073-3091.
Lennon, G., et al., "The I.M.A.G.E. Consortium: an Integrated Molecular Analysis of Genomes and Their Expression," Genomics (1996) 33:151-152.
Lockhart, D.J., et al., "Expression monitoring by hybridization to high-density oligonuleotide arrays," Nature Biotechnology (1996) vol. 14: 1675-1680.
Marte, B.M., et al., "R-Ras can activate the phosphoinositide 3-kinase but not the MAP kinase arm of the Ras effector pathways," Current Biology (1996) vol. 7:63-70.

Masure, S., et al., "Molecular cloning, expression and characterization of the human serine/threonine kinase Akt-3," Eur. J. Biochem. (1999) vol. 265:353-360.
Meier, R., et al., "Mitogenic Activation, Phosphorylation, and Nuclear Transloction of Protein Kinase Bβ*," Journal of Biological Chemistry (1997) vol. 272 (48) 30491-30497.
Meredith, J.E., "The Extracellular Matrix as a Cell Survival Factor," Molecular Biology of the Cell, (1993) vol. 4 953-961.
Mitelman, F., "A breakpoint map of recurrent chromosomal rearrangements in human neoplasia," Nature Genetics (1997) 15:417-474.
Musacchio, A., "The PH domain: a common piece in the structural patchwork of signalling proteins," Trends Biochem Sci 1993 18:343-348.
Nakatani, K., "Identification of a Human Akt3 (Protein Kinase Bγ) Which Contains the Regulatory Serine Phosphorylation Site," Biochemical and Biophysical Research (1999) vol. 257:906-910.
Nakatani, K., "Up-regulation of Akt3 in Estrogen Receptor-deficient Breast Cancers and Androgen-independent Prostate Cancer Lines*," Journal of Biological Chemistry (1999) vol. 274:21528-21532.
Okano, H., "Myelin Basic Protein Gene and the Function of Antisense RNA in its Repression in Myelin-Deficient Mutant Mouse," Journal of Neurochemistry (1991) vol. 56:560-567.
Shepherd, P.R., et al., "Phosphoinositide 3-kinase: the key switch mechanism in insulin signalling," Biochem. Journal (1998) vol. 333:471-490.
Staal, S.P., "Molecular cloning of the akt oncogene and its human homologues AKT1 and AKT2: Amplification of AKT1 in a primary human gastric adenocarcinoma," Proc. Natl. Acad. Sci USA (1987) vol. 84:5034-5037.
Stokoe, D., et al, "Dual Role of Phosphatidylinositol-3,4,5-trisphosphate in the Activation of Protein Kinase B," Science (1997) vol. 277:567-570.
Walker, K.S., et al., "Activation of protein kinase B β and γ isoforms by insulin in vivo and by 3-phosphoinositide-dependent protein kinase-1 in vitro: comparison with protein kinase B α," Biochem Journal (1998) vol. 331:299-308.
Stephens, L., et al. "Protein Kinase B Kinases That Mediate Phosphatidylinositol 3,4,5-Trisphosphate Dependent Activation of Protein Kinase B", Science (1998) vol. 279:710-714.
Marte, B.M., et al., "PKB/Akt: connecting phosphoinositide 3-kinase to cell survival and beyond," TIBS (1997) 22:355-358.
EMBL: AF135794 Apr. 9, 1999.
EMBL: AF124141 May 7, 1999.
EMBL: AF124142 May 7, 1999.
EMBL: AJ245709 Aug. 27, 1999.
EMBL: D49836 Dec. 29, 1995.
EMBL: AL117525 Sep. 15, 1999.
Coffer, P.J., et al., "Protein kinase B (c-akt): a multifunctional mediator of phosphatidylinositol 3-kinase activation", Biochem Journal 1998 vol. 335:1-13.
Dudek, H., et al., "Regulation of Neuronal Survival by the Serine-Threonine Protein Kinase Akt," Science (1997) 275:661-665.
Philpott, K.L., "Activated Phosphatidylinositol 3-Kinase and Akt Kinase Promote Survival of Superior Cervical Neurons," Journal of Cell Biology (1997) vol. 139 (3) 809-815.

```
                   M  S  D  V  T  I  V  K  E  G  W  V  Q  K  R  G  E     17
   1   GGGAGTCATCATGAGCGATGTTACCATTGTGAAAGAAGGTTGGGTTCAGAAGAGGGAGA
             Y  I  K  N  W  R  P  R  Y  F  L  L  K  T  D  G  S  F  I  G   37
  61   ATATATAAAAAACTGGAGGCCAAGATACTTCCTTTTGAAGACAGATGGCTCATTCATAGG
             Y  K  E  K  P  Q  D  V  D  L  P  Y  P  L  N  N  F  S  V  A   57
 121   ATATAAAGAGAAACCTCAAGATGTGGATTTACCTTATCCCCTCAACAACTTTTCAGTGGC
             K  C  Q  L  M  K  T  E  R  P  K  P  N  T  F  I  I  R  C  L   77
 181   AAAATGCCAGTTAATGAAAACAGAACGACCAAAGCCAAACACATTTATAATCAGATGTCT
             Q  W  T  T  V  I  E  R  T  F  H  V  D  T  P  E  E  R  E  E   97
 241   CCAGTGGACTACTGTTATAGAGAGAACATTTCATGTAGATACTCCAGAGGAAAGGGAAGA
             W  T  E  A  I  Q  A  V  A  D  R  L  Q  R  Q  E  E  E  R  M  117
 301   ATGGACAGAAGCTATCCAGGCTGTAGCAGACAGACTGCAGAGGCAAGAAGAGGAGAGAAT
             N  C  S  P  T  S  Q  I  D  N  I  G  E  E  E  M  D  A  S  T  137
 361   GAATTGTAGTCCAACTTCACAAATTGATAATATAGGAGAGGAAGAGATGGATGCCTCTAC
             T  H  H  K  R  K  T  M  N  D  F  D  Y  L  K  L  L  G  K  G  157
 421   AACCCATCATAAAAGAAAGACAATGAATGATTTTGACTATTTGAAACTACTAGGTAAAGG
             T  F  G  K  V  I  L  V  R  E  K  A  S  G  K  Y  Y  A  M  K  177
 481   CACTTTTGGGAAAGTTATTTTGGTTCGAGAGAAGGCAAGTGGAAAATACTATGCTATGAA
             I  L  K  K  E  V  I  I  A  K  D  E  V  A  H  T  L  T  E  S  197
 541   GATTCTGAAGAAAGAAGTCATTATTGCAAAGGATGAAGTGGCACACACTCTAACTGAAAG
             R  V  L  K  N  T  R  H  P  F  L  T  S  L  K  Y  S  F  Q  T  217
 601   CAGAGTATTAAAGAACACTAGACATCCCTTTTTAACATCCTTGAAATATTCCTTCCAGAC
             K  D  R  L  C  F  V  M  E  Y  V  N  G  E  L  F  F  H  L  237
 661   AAAAGACCGTTTGTGTTTTGTGATGGAATATGTTAATGGGGGCGAGCTGTTTTTCCATTT
             S  R  E  R  V  F  S  E  D  R  T  R  F  Y  G  A  E  I  V  S  257
 721   GTCGAGAGAGCGGGTGTTCTCTGAGGACCGCACACGTTTCTATGGTGCAGAAATTGTCTC
             A  L  D  Y  L  H  S  G  K  I  V  Y  R  D  L  K  L  E  N  L  277
 781   TGCCTTGGACTATCTACATTCCGGAAAGATTGTGTACCGTGATCTCAAGTTGGAGAATCT
             M  L  D  K  D  G  H  I  K  I  T  D  F  G  L  C  K  E  G  I  297
 841   AATGCTGGACAAAGATGGCCACATAAAAATTACAGATTTTGGACTTTGCAAAGAAGGGAT
                                        *
             T  D  A  A  T  M  K  T  F  C  G  T  P  E  Y  L  A  P  E  V  317
 901   CACAGATGCAGCCACCATGAAGACATTCTGTGGCACTCCAGAATATCTGGCACCAGAGGT
             L  E  D  N  D  Y  G  R  A  V  D  W  W  G  L  G  V  V  M  Y  337
 961   GTTAGAAGATAATGACTATGGCCGAGCAGTAGACTGGTGGGGCCTAGGGGTTGTCATGTA
             E  M  M  C  G  R  L  P  F  Y  N  Q  D  H  E  K  L  F  E  L  357
1021   TGAAATGATGTGTGGGAGGTTACCTTTCTACAACCAGGACCATGAGAAACTTTTTGAATT
             I  L  M  E  D  I  K  F  P  R  T  L  S  S  D  A  K  S  L  L  377
1081   AATATTAATGGAAGACATTAAATTTCCTCGAACACTCTCTTCAGATGCAAAATCATTGCT
             S  G  L  L  I  K  D  P  N  K  R  L  G  G  P  D  D  A  K  397
1141   TTCAGGGCTCTTGATAAAGGATCCAAATAAACGCCTTGGTGGAGGACCAGATGATGCAAA
             E  I  M  R  H  S  F  F  S  G  V  N  W  Q  D  V  Y  D  K  K  417
1201   AGAAATTATGAGACACAGTTTCTTCTCTGGAGTAAACTGGCAAGATGTATATGATAAAAA
             L  V  P  P  F  K  P  Q  V  T  S  E  T  D  T  R  Y  F  D  E  437
1261   GCTTGTACCTCCTTTTAAACCTCAAGTAACATCTGAGACAGATACTAGATATTTTGATGA
             E  F  T  A  Q  T  I  T  I  T  P  P  E  K  Y  D  E  D  G  M  457
1321   AGAATTTACAGCTCAGACTATTACAATAACACCACCTGAAAAATATGATGAGGATGGTAT
                                                          *
             D  C  M  D  N  E  R  R  P  H  F  P  Q  F  S  Y  S  A  S  G  477
1381   GGACTGCATGGACAATGAGAGGCGGCCGCATTTCCCTCAATTTTCCTACTCTGCAAGTGG
             R  E                                                          479
1441   ACGAGAATAAGTCTCTTTCATTCTGCTACTTCACTGTCATCTTCAATTTATTACTGAAAA

1501   TGATTCCTGGACATCACCAGTCCTAGCTCTTACACATAGCAGGGGCA
```

```
Akt-1 : MSDVAIVKEGWLHKRGEYIKTWRPRYFLLKNDGTFIGYKERPQDVDQREAPLNNFSVAQCQLMKTERPRPNTFIIRCLQWTTVIERTFHV : 90
Akt-2 : MNEVSVIKEGWLHKRGEYIKTWRPRYFLLKSDGSFIGYKERPEAPDQTLPPLNNFSVAECQLMKTERPPNTFVIRCLQWTTVIERTFHV : 90
Akt-3 : MSDVTIVKEGWVQKRGEYIKNWRRPYFLLKTDGSFIGYKEKPQDVDLP-YPLNNFSVAKCQLMKTERPKPNTFIIRCLQWTTVIERTFHV : 89

Akt-1 : ETPEEREEWTTAIQTVADGLKKQE--EEEMDFRSGSPSDNSGAEEMEVSLAKPKHRVTMNEPEYLKLLLGKGTFGKVILVKEKATGRYYAM : 178
Akt-2 : DSPDEREEWMRAIQMVANSLKQRAPGEDPMDYKCGSPSDSSTTEEMEVAVSKARAKVTMNDPDYLKLLLGKGTFGKVILVREKATGRYYAM : 180
Akt-3 : DTPEEREEWTEAIQAVADRLQRE---EERMNCSPTSQIDNIGEEEMDASTTHHK-RKTMNDPDYLKLLLGKGTFGKVILVREKASGKYYAM : 176

Akt-1 : KILKKEVIVAKDEVAHTLTENRVLQNSRHPFLTALKYSFQTIHDRLCFVMEYANGGELFFHLSRERVFSEDRARFYGAEIVSALDYLHSEK : 268
Akt-2 : KILRKEVIIAKDEVAHTLTESRVLQNTRHPFLTALKYAFQTHDRLCFVMEYANGGELFFHLSRERVFTEERARFYGAEIVSALEYLHS-R : 269
Akt-3 : KILKKEVIVAKDEVAHTLTENRVLKNSRHPFLTSLKYSFQTIKDRLCFVMEYVNGGELFFHLSRERVFSEDRTRFYGAEIVSALDYLHS-G : 265

Akt-1 : NVVYRDLKLENLMLDKDGHIKITDFGLCKEGIKDGATMKTFCGTPEYLAPEVLEDNDYGRAVDWWGLGVVMYEMMCGRLPFYNQDHEKLF : 358
Akt-2 : DVVYRDLKLENLMLDKDGHIKITDFGLCKEGISDGATMKTFCGTPEYLAPEVLEDNDYGRAVDWWGLGVVMYEMMCGRLPFYNQDHERLF : 359
Akt-3 : KIVYRDLKLENLMLDKDGHIKITDFGLCKEGITDAATMKTFCGTPEYLAPEVLEDNDYGRAVDWWGLGVVMYEMMCGRLPFYNQDHEKLF : 355

Akt-1 : ELILMEEIRFPRTLGPEAKSLLSGLLKKDPKQRLGGGSEDAKEIMQHRFFAGIVWQHVYEKKLSPPFKPQVTSETDTRYFDEEFTAQMIT : 448
Akt-2 : ELILMEEIRFPRTLSPEAKSLLAGLLKKDPKQRLGGGPSDAKEVMEHRFFLSINWQDVVQKKLLPPFKPQVTSEVDTRYFDDEFTAQSIT : 449
Akt-3 : ELILMEDIKFPRTLSSDAKSLLSGLLIKDPNKRLGGGPDDAKEIMRHSFFSGVNWQDVYDKKLVPPFKPQVTSETDTRYFDEEFTAQTIT : 445

Akt-1 : ITPPDQDDS--MECVDSERRPHFPQFSYSASGTA : 480
Akt-2 : ITPPDRYDS--LGLLELDQRTHFPQFSYSASIRE : 481
Akt-3 : ITPPEKYDEDGMDCMDNERRPHFPQFSYSASGRE : 479
```

A
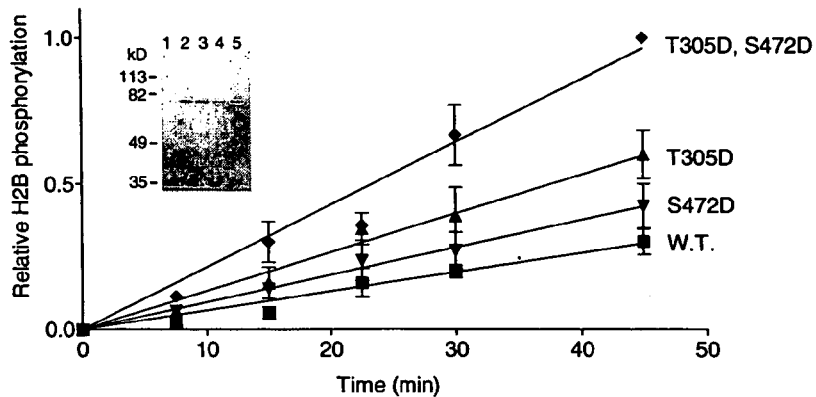
B
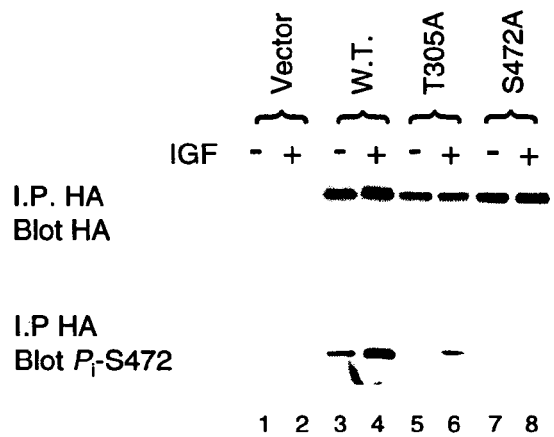
C
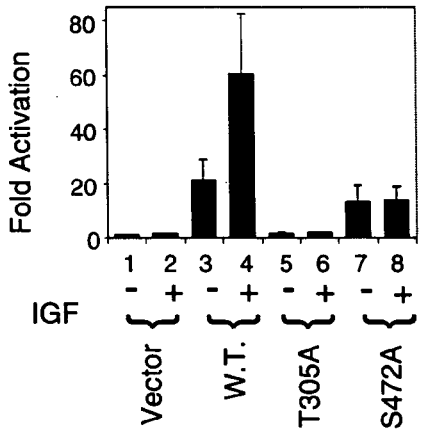
Figure 3

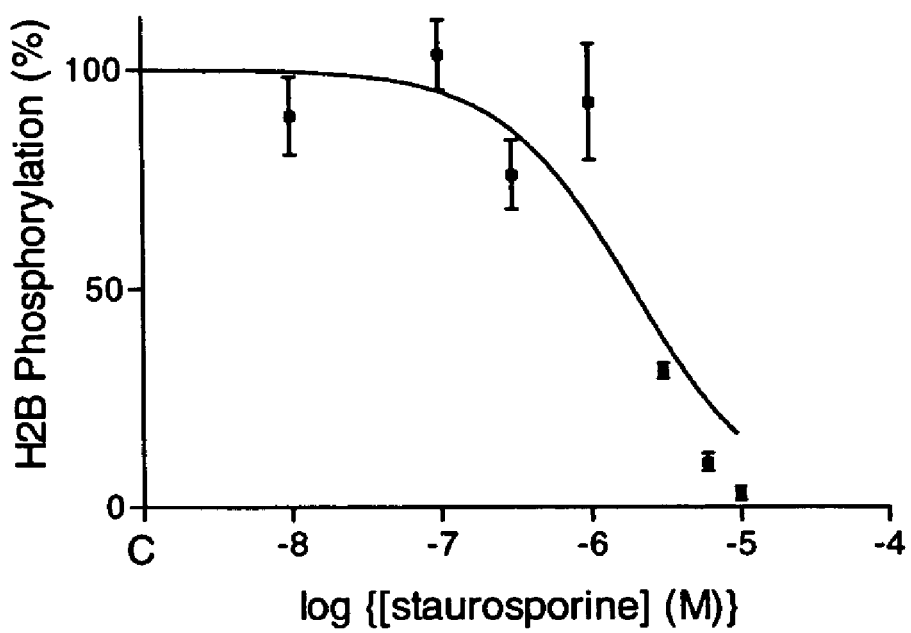
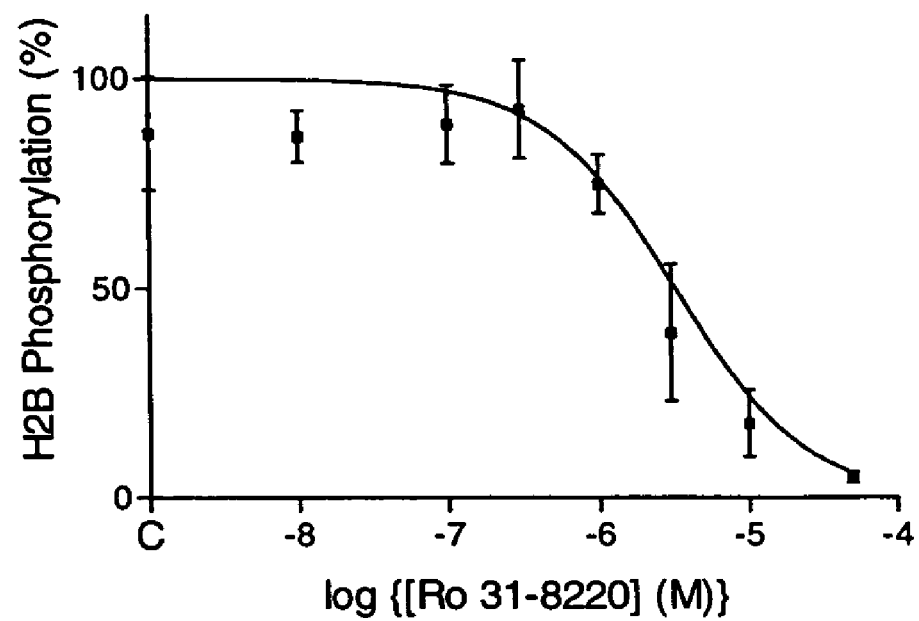
Figure 4.

HUMAN AKT-3

This application is a national stage filing of International Publication No. WO/00/37613 filed Dec. 17, 1999 which claims priority from Great Britain Patent Application No. 9828375.7 filed Dec. 22, 1998 and entitled "Human AKT-3".

FIELD OF THE INVENTION

The present invention is concerned with cloning and expression of a new human serine/threonine kinase termed "Akt-3" and, in particular, with nucleic acid molecules encoding the Akt-3 protein, the protein itself and compounds which can be used to inhibit cell survival.

BACKGROUND OF THE INVENTION

A characteristic feature of many cancer cells is their ability to grow independently of adhesion. In contrast, when untransformed endothelial cells are prevented from adhering to the extracellular matrix (ECM), they undergo apoptosis (Frisch & Francis, 1994; Meredith et al, 1993). The process by which normally adherent cells are triggered to undergo apoptosis when they are unable to adhere to ECM has been termed "anoikis" (Frisch & Ruoslahti, 1997) and is an example of the effect on a cell of removal of a survival factor. Changes in signalling by adhesion molecules can lead to resistance to anoikis (Frisch & Ruoslahti, 1997) and this may contribute to the mechanism whereby cancer cells that grow independently of adhesion are able to avoid anoikis.

Akt (also known as protein kinase B (PKB) or "related to A and C protein kinase" (RAC-PK)) is a serine/threonine kinase that has been implicated in regulating cell survival (Khwaja et al., 1997; Dudek et al., 1997; Kauffmann-Zeh et al., 1997; Kennedy et al., 1997; Datta et al., 1997; Marte & Downward, 1997). Akt can inhibit apoptosis induced by detachment from ECM (Khwaja et al., 1997), as well as by survival factor withdrawal (Kennedy et al., 1997; Ahmed et al., 1997; Dudek et al., 1997; Kauffman-Zeh et al., 1997; Philpott et al., 1997; Crowder & Freeman, 1998; Eves et al., 1998) or irradiation (Kulik et al., 1997).

Akt comprises an $NH_2$-terminal pleckstrin homology (PH) domain involved in lipid binding, a kinase domain and a COOH-terminal "tail". Akt is thought to be activated by recruitment to the plasma membrane and subsequent phosphorylation by two upstream kinases, PDK-1 and PDK-2 (reviewed in Coffer et al, 1998; Alessi & Cohen, 1998). The binding of 3-phosphoinositides, generated by phosphatidylinositol 3-kinase (PI 3-kinase), to the PH domain of Akt is believed to promote translocation to the plasma membrane and to facilitate phosphorylation of Akt-1 by PDK-1 at $Thr^{308}$ (Alessi et al., 1996; Alessi et al., 1997; Stephens et al., 1998) or of Akt-2 at $Thr^{309}$ (Meier et al., 1997). In addition to phosphorylation of $Thr^{308}{}_1$ full activation requires phosphorylation of the COOH tail at $Ser^{473}$ in Akt-1 (Alessi et al, 1996) or at $Ser^{474}$ in Akt-2 (Meier et al., 1997). The enzyme responsible for phosphorylation of $Ser^{473}/Ser^{474}$ was originally named PDK-2 but recently the integrin-linked kinase, ILK (Delcommenne et al., 1998) has emerged as a candidate for this function.

Two human isoforms of Akt have been described to date, Akt-1 and Akt-2 (Coffer & Woodgett, 1991; Jones et al., 1991; Cheng et al., 1992). A third isoform, here referred to as Akt-3, has been described in the rat (Konishi et al., 1995). Since this rat Akt-3 possesses an apparently truncated tail and thereby lacks $Ser^{473}$, its regulation may differ from that of Akt-1 and Akt-2. Both Akt-1 and Akt-2 are expressed widely, although the expression of Akt-2 is most prominent in insulin-responsive tissues, such as liver and skeletal muscle (Konishi et al., 1994; Altomare et al., 1995). Akt-1 and Akt-2 are activated by insulin in rat adipocytes, hepatocytes and skeletal muscle. In contrast, Akt-3 does not appear to be strongly activated by insulin in these tissues (Walker et al., 1998). The role of the various Akt isoforms in insulin signalling may limit the utility of compounds that inhibit Akt-1 or Akt-2 activity as such agents may induce symptoms observed in patients with diabetes. We hypothesized that this problem may be avoided by using selective inhibitors of Akt-3 and this prompted us to identify the human analogue of rat Akt-3.

DETAILED DESCRIPTION OF THE INVENTION

The present inventors have now identified and characterised a nucleic acid molecule that encodes the human isoform of Akt-3. Significantly, human Akt-3 possesses a COOH-terminal tail that contains an amino acid residue analogous to $Ser^{473}/Ser^{474}$ previously implicated in the activation of Akt-1/Akt-2, but absent in the rat Akt-3 protein.

Therefore, there is provided by a first aspect of the present invention a nucleic acid molecule encoding human Akt-3 or a functional equivalent, derivative or bioprecursor thereof, comprising the amino acid sequence illustrated in FIG. 2 (and as SEQ ID NO:3). Preferably, the molecule is a DNA molecule and even more preferably a cDNA molecule, and even more preferably comprises the sequence of nucleotides provided in FIG. 1 (SEQ ID NO:1). Also provided by this aspect of the invention is a nucleic acid molecule capable of hybridising to the molecule according to the invention under high stringency conditions.

Stringency of hybridisation as used herein refers to conditions under which polynucleic acids are stable. The stability of hybrids is reflected in the melting temperature (Tm) of the hybrids. Tm can be approximated by the formula:

$$81.5° C.+16.6(\log_{10}[Na^+]+0.41 \text{ (\% } G\&C)-600/l$$

wherein 1 is the length of the hybrids in nucleotides. Tm decreases approximately by 1–1.5° C. with every 1% decrease in sequence homology.

The term "stringency" refers to the hybridisation conditions wherein a single-stranded nucleic acid joins with a complementary strand when the purine or pyrimidine bases therein pair with their corresponding base by hydrogen bonding. High stringency conditions favour homologous base pairing whereas low stringency conditions favour non-homologous base pairing.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration, for example 1M NaCl.

"High stringency" conditions comprise, for example, a temperature of about 42° C. or less, a formamide concentration of less than about 20%, and a low salt (SSC) concentration; or, alternatively, a temperature of about 65° C., or less, and a low salt (SSPE) concentration. For example, high stringency conditions comprise hybridization in 0.5 M $NaHPO_4$, 7% sodium dodecyl sulfate (SDS), 1 mM EDTA at 65° C. (Ausubel, F. M. et al. *Current Protocols in Molecular Biology*, Vol. I, 1989; Green Inc. New York, at 2.10.3).

"SSC" comprises a hybridization and wash solution. A stock 20×SSC solution contains 3M sodium chloride, 0.3M sodium citrate, pH 7.0.

"SSPE" comprises a hybridization and wash solution. A 1×SSPE solution contains 180 mM NaCl, 10 mM NaH$_2$PO4 and 1 mM EDTA, pH 7.4.

The nucleic acid capable of hybridising to nucleic acid molecules according to the invention will generally be at least 85%, preferably at least 90% and even more preferably at least 95% homologous to the nucleotide sequences according to the invention.

The DNA molecules according to the invention may, advantageously, be included in a suitable expression vector to express polypeptides encoded therefrom in a suitable host.

The present invention also comprises within its scope proteins or polypeptides encoded by the nucleic acid molecules according to the invention or a functional equivalent, derivative or bioprecursor thereof.

An expression vector according to the invention includes a vector having a nucleic acid according to the invention operably linked to regulatory sequences, such as promoter regions, that are capable of effecting expression of said DNA fragments. The term "operably linked" refers to a juxta position wherein the components described are in a relationship permitting them to function in their intended manner. Such vectors may be transformed into a suitable host cell to provide for expression of a polypeptide according to the invention. Thus, in a further aspect, the invention provides a process for preparing polypeptides according to the invention which comprises cultivating a host cell, transformed or transfected with an expression vector as described above under conditions to provide for expression by the vector of a coding sequence encoding the polypeptides, and recovering the expressed polypeptides.

The vectors may be, for example, plasmid, virus or phage vectors provided with an origin of replication, optionally a promoter for the expression of said nucleotide and optionally a regulator of the promoter. The vectors may contain one or more selectable markers, such as, for example, ampicillin resistance.

Regulatory elements required for expression include promoter sequences to bind RNA polymerase and transcription initiation sequences for ribosome binding. For example, a bacterial expression vector may include a promoter such as the lac promoter and for transcription initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art.

A nucleic acid molecule according to the invention may be inserted into the vectors described in an antisense orientation in order to provide for the production of antisense RNA. Antisense RNA or other antisense nucleic acids may be produced by synthetic means.

In accordance with the present invention, a defined nucleic acid includes not only the identical nucleic acid but also any minor base variations including in particular, substitutions in bases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The present invention also advantageously provides nucleic acid sequences of at least approximately 10 contiguous nucleotides of a nucleic acid according to the invention and preferably from 10 to 120, and even more preferably from 10 to approximately 50 nucleotides. These sequences may, advantageously be used as probes or primers to initiate replication, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting for the presence of any duplex or triplex formation between the probe and any nucleic acid in the sample.

According to the present invention these probes may be anchored to a solid support. Preferably, they are present on an array so that multiple probes can simultaneously hybridize to a single biological sample. The probes can be spotted onto the array or synthesised in situ on the array. (See Lockhart et al., Nature Biotechnology, vol. 14, December 1996 "Expression monitoring by hybridisation to high density oligonucleotide arrays"). A single array can contain more than 100, 500 or even 1,000 different probes in discrete locations.

Advantageously, the nucleic acid sequences, according to the invention may be produced using such recombinant or synthetic means, such as for example using PCR cloning mechanisms which generally involve making a pair of primers, which may be from approximately 10 to 50 nucleotides to a region of the gene which is desired to be cloned, bringing the primers into contact with mRNA, cDNA, or genomic DNA from a human cell, performing a polymerase chain reaction under conditions which bring about amplification of the desired region, isolating the amplified region or fragment and recovering the amplified DNA. Generally, such techniques as defined herein are well known in the art, such as described in Sambrook et al (Molecular Cloning: a Laboratory Manual, 1989).

The nucleic acids or oligonucleotides according to the invention may carry a revealing label. Suitable labels include radioisotopes such as $^{32}$P or $^{35}$S, enzyme labels or other protein labels such as biotin or fluorescent markers. Such labels may be added to the nucleic acids or oligonucleotides of the invention and may be detected using known techniques per se.

A further aspect of the invention comprises human Akt-3 or a functional equivalent, derivative or bioprecursor thereof, comprising an amino acid sequence as illustrated in FIG. 2.

The polypeptide designated human Akt-3 according to the invention includes all possible amino acid variants encoded by the nucleic acid molecule according to the invention including a polypeptide encoded by said molecule and having conservative amino acid changes. Polypeptides according to the invention further include variants of such sequences, including naturally occurring allelic variants which are substantially homologous to said polypeptides. In this context, substantial homology is regarded as a sequence which has at least 90% amino acid homology with the polypeptides encoded by the nucleic acid molecules according to the invention and even more preferably at least 95% amino acid homology.

The nucleic acid molecule or the human Akt-3 according to the invention may, advantageously, be used as a medicament or in the preparation of a medicament, for treating disease associated with Akt-3 activity such as, cancer or the like.

Advantageously, the nucleic acid molecule or the polypeptide according to the invention may be provided in a pharmaceutical composition together with a pharmaceutically acceptable carrier, diluent or excipient therefor.

The present invention is further directed to inhibiting Akt-3 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature protein sequence, which encodes for the protein of the present invention, is used to design an antisense RNA oligonucleotide of from 10 to 40 base pairs in length. A DNA oligonucleotide is designed to be complementary to a region of the gene involved in transcription (triple-helix—see Lee et al. Nucl. Acids Res., 6:3073 (1979); Cooney et al., Science, 241:456 (1988); and Dervan et al., Science, 251: 1360 (1991), thereby preventing transcription and the production of Akt-3. The antisense RNA oligonucleotide hybridises to the mRNA in vivo and blocks translation of an mRNA molecule into the Akt-3 (antisense—Okano, J. Neurochem., 56:560 (1991); Oligodeoxynucleotides as Antisense Inhibitors of Gene Expression, CRC Press, Boca Raton, Fla. (1998)).

Alternatively, the oligonucleotide described above can be delivered to cells by procedures in the art such that the anti-sense RNA or DNA may be expressed in vivo to inhibit production of Akt-3 in the manner described above.

Antisense constructs to Akt-3, therefore, may inhibit the survival of the cell and prevent further cancer or tumour growth.

According to a further aspect of the invention there is also provided a transgenic cell, tissue or organism comprising a transgene capable of expressing human Akt-3 protein according to the invention. The term "transgene capable of expression" as used herein means a suitable nucleic acid sequence which leads to expression of human Akt-3 or human proteins having the same function and/or activity. The transgene, may include, for example, genomic nucleic acid isolated from human cells or synthetic nucleic acid, including DNA integrated into the genome or in an extrachromosomal state. Preferably, the transgene comprises the nucleic acid sequence encoding the proteins according to the invention as described herein, or a functional fragment of said nucleic acid. A functional fragment of said nucleic acid should be taken to mean a fragment of the gene comprising said nucleic acid coding for the proteins according to the invention or a functional equivalent, derivative or a non-functional derivative such as a dominant negative mutant, or bioprecursor of said proteins. For example, it would be readily apparent to persons skilled in the art that nucleotide substitutions or deletions may be used using routine techniques, which do not affect the protein sequence encoded by said nucleic acid, or which encode a functional protein according to the invention.

Human Akt-3 protein expressed by said transgenic cell, tissue or organism or a functional equivalent or bioprecursor of said protein also form part of the present invention.

Antibodies to human Akt-3 may, advantageously, be prepared by techniques which are known in the art. For example, polyclonal antibodies may be prepared by inoculating a host animal, such as a mouse, with human Akt-3 according to the invention or an epitope thereof and recovering immune serum. Monoclonal antibodies may be prepared according to known techniques such as described by Kohler R. and Milstein C., Nature (1975) 256, 495–497.

Antibodies according to the invention may also be used in a method of detecting for the presence of human Akt-3 according to the invention, which method comprises reacting the antibody with a sample and identifying any protein bound to said antibody. A kit may also be provided for performing said method which comprises an antibody according to the invention and means for reacting the antibody with said sample.

Proteins which interact with the polypeptide of the invention may be identified by, for example, investigating protein—protein interactions using the two-hybrid vector system first proposed by Chien et al (1991). Proc. Natl. Acad. Sci. USA 88: 9578–9582.

This technique is based on functional reconstitution in vivo of a transcription factor which activates a reporter gene. More particularly the technique comprises providing an appropriate host cell with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or said activating domain of the transcription factor, expressing in the host at least one second hybrid DNA sequence, such as a library or the like, encoding putative binding proteins to be investigated together with the DNA binding or activating domain of the transcription factor which is not incorporated in the first fusion; detecting any binding of the proteins to be investigated with a protein according to the invention by detecting for the presence of any reporter gene product in the host cell; optionally isolating second hybrid DNA sequences encoding the binding protein.

An example of such a technique utilises the GAL4 protein in yeast. GAL4 is a transcriptional activator of galactose metabolism in yeast and has a separate domain for binding to activators upstream of the galactose metabolising genes as well as a protein binding domain. Nucleotide vectors may be constructed, one of which comprises the nucleotide residues encoding the DNA binding domain of GAL4. These binding domain residues may be fused to a known protein encoding sequence, such as for example the nucleic acids according to the invention. The other vector comprises the residues encoding the protein binding domain of GAL4. These residues are fused to residues encoding a test protein. Any interaction between polypeptides encoded by the nucleic acid according to the invention and the protein to be tested leads to transcriptional activation of a reporter molecule in a GAL-4 transcription deficient yeast cell into which the vectors have been transformed. Preferably, a reporter molecule such as β-galactosidase is activated upon restoration of transcription of the yeast galactose metabolism genes.

A further aspect of the invention provides a method of identifying compounds which selectively inhibit human Akt-3 mediated promotion of cell survival said method comprising i) providing a cell transformed with an expression vector activating the Akt-3 pathway which cell survives in the presence or absence of a survival factor compared to a control cell which has not been transformed with said vector and will die in the absence of said survival factor ii) contacting said cells with a test compound following removal of said cells from said survival factors, wherein death of said transformed cell is indicative of selective inhibition of said compound on the survival promoting human Akt-3 pathway.

Alternatively, the survival promoting activity of Akt-3 could be assessed by i) providing a cell transformed with an expression vector activating the Akt-3 pathway in addition to a control cell which has not been transformed with said vector, ii) contacting each of said cells with a death inducing agent, whereby death of said control cell and survival of said transformed cell is indicative of the survival promoting activity of the activated Akt-3 pathway, iii) subsequently contacting said transformed cell without removal of said death inducing agent, with a test compound, wherein death of said cell is indicative of selective inhibition of said compound on the survival promoting human Akt-3 pathway.

In a further aspect the present invention provides methods to identify agents that affect the activity of the human Akt-3 protein, comprising contacting said protein with a substrate, regulatory molecule or surrogate thereof and monitoring the interaction with the test substance using standard phosphorylation or binding assays well known in the art.

Compounds which are identified according to this aspect of the invention in addition to antibodies to the human Akt-3 may, advantageously, be utilised as a medicament or alternatively in the preparation of a medicament for treating diseases associated with expression of human Akt-3 protein according to the invention.

A further aspect of the invention provides a pharmaceutical composition comprising any of a compound, an antisense molecule or an antibody according to the invention together with a pharmaceutically acceptable carrier, diluent or excipient therefor.

The antisense molecules or indeed the compounds identified as agonists or antagonists of the nucleic acids or polypeptides according to the invention may be used in the form of a pharmaceutical composition, which may be prepared according to procedures well known in the art. Preferred compositions include a pharmaceutically acceptable vehicle or diluent or excipient, such as for example, a physiological saline solution. Other pharmaceutically acceptable carriers including other non-toxic salts, sterile water or the like may also be used. A suitable buffer may also be present allowing the compositions to be lyophilized and stored in sterile conditions prior to reconstitution by the addition of sterile water for subsequent administration. Incorporation of the polypeptides of the invention into a solid or semi-solid biologically compatible matrix may be carried out which can be implanted into tissues requiring treatment.

The carrier can also contain other pharmaceutically acceptable excipients for modifying other conditions such as pH, osmolarity, viscosity, sterility, lipophilicity, solubility or the like.

Pharmaceutically acceptable excipients which permit sustained or delayed release following administration may also be included.

The polypeptides, the nucleic acid molecules or compounds according to the invention may be administered orally. In this embodiment they may be encapsulated and combined with suitable carriers in solid dosage forms which would be well known to those skilled in the art.

As would be well known to those of skill in the art, the specific dosage regime may be calculated according to the body surface area of the patient or the volume of body space to be occupied, dependent upon the particular route of administration to be used. The amount of the composition actually administered will, however, be determined by a medical practitioner, based on the circumstances pertaining to the disorder to be treated, such as the severity of the symptoms, the composition to be administered, the age, weight, and response of the individual patient and the chosen route of administration.

BRIEF DESCRIPTION OF THE FIGURES

The present invention may be more clearly understood with reference to the following example which is purely exemplary and the accompanying drawings wherein:

FIG. 1 is an illustration of the cDNA sequence (SEQ ID NO: 1) and deduced amino acid sequence (SEQ ID NO: 3) of human Akt-3. The Akt-3 coding sequence and parts of the 5' and 3' untranslated regions are shown and numbered in the left hand column. The deduced amino acid sequence of the Akt-3 protein is shown above the corresponding DNA sequence and is numbered in the right hand column. The two amino acid residues that are presumed to be phosphorylated upon activation of Akt-3 (Thr$^{305}$ and Ser$^{472}$ are in bold and marked with an asterisk. The COOH-terminal part of the human Akt-3 protein that differs with the rat homologue is underlined.

FIG. 2 is an alignment of the deduced amino acid sequences for human Akt-1 (SEQ ID NO: 15), Akt-2 (SEQ ID NO: 16) and Akt-3 (SEQ ID NO: 3). The sequences were aligned using the ClustalW alignment program (EMBL, Heidelberg, Germany). Amino acid residues conserved between all three proteins are included in the black areas. Residues conserved between only two of the sequences are shaded in grey. Amino acid residues are numbered in the right hand column. The conserved Thr and Ser residues that are presumed to be phosphorylated upon activation are marked with an asterisk above the sequence.

FIG. 3 is an illustration of phosphorylation of histone H2B by Akt-3 variants. (A) Akt-3 was expressed as a GST fusion protein in E. Coli. To assess hAkt-3 activity, Histone H2B was incubated with GST-Akt-3 and GST-Akt-3 variants for the indicated time and the extent of phosphorylation assessed after SDS-PAGE. The variants of Akt-3 are designated: W.T., wild type; T305D, Thr$^{305}$ mutated to Asp; S472D, Ser$^{472}$ mutated to Asp; T305D,S472D, both Thr$^{305}$ and Ser$^{472}$ mutated to Asp. No significant phosphorylation was observed when GST was used in place of GST-Akt. The results are the mean (±s.e.m.; n=3 to 6) and are expressed relative to the extent of phosphorylation of H2B catalysed by T305D, S472D hAkt-3 after 45 minutes. (B) HEK-293 cells were transfected with either vector (lanes 1 & 2) or Akt-3 (lanes 3 and 4) AKt-3T305A (lanes 5 & 6) or Akt-3 S472A (lanes 7 and 8) and either treated with buffer (lanes 1, 3 5 and 7) or IGF-1 (50 ng/ml; lanes 2, 4, 6 and 8). Akt-3 was immunoprecipitated with antibody 3F10 (anti-HA tag). Samples were analysed by blotting for the HA-tag (upper panel) or with a phosphospecific antibody which recognises phosphorylated ser$^{472}$ (lower panel). (C) Akt activity in HA-immuno-precipitates from samples prepared as described above was assessed by measuring phosphorylation of a peptide substrate (Crosstide). The results are expressed as the increase in activity compared to unstimulated cells transfected with empty vector (mean±s.e.m., n=7).

FIG. 4 is an illustration of inhibition of Akt-3 by staurosporine and RO 31-8220. Histone H2B was treated with Akt-3 (T305D,S472D variant) in the presence of the indicated concentrations of either staurosporine or RO 31-8220. After 30 minutes, the reaction was terminated and the extent of H2B phosphorylation quantified on a phosphorimager following SDS-PAGE. The results (mean±s.e.m., n=3) are expressed as relative to (%) the phosphorylation observed in the presence of solvent (control, "C").

EXAMPLES

Materials and Methods

Oligonucleotide Synthesis and DNA Sequence Determination

Figure 5:
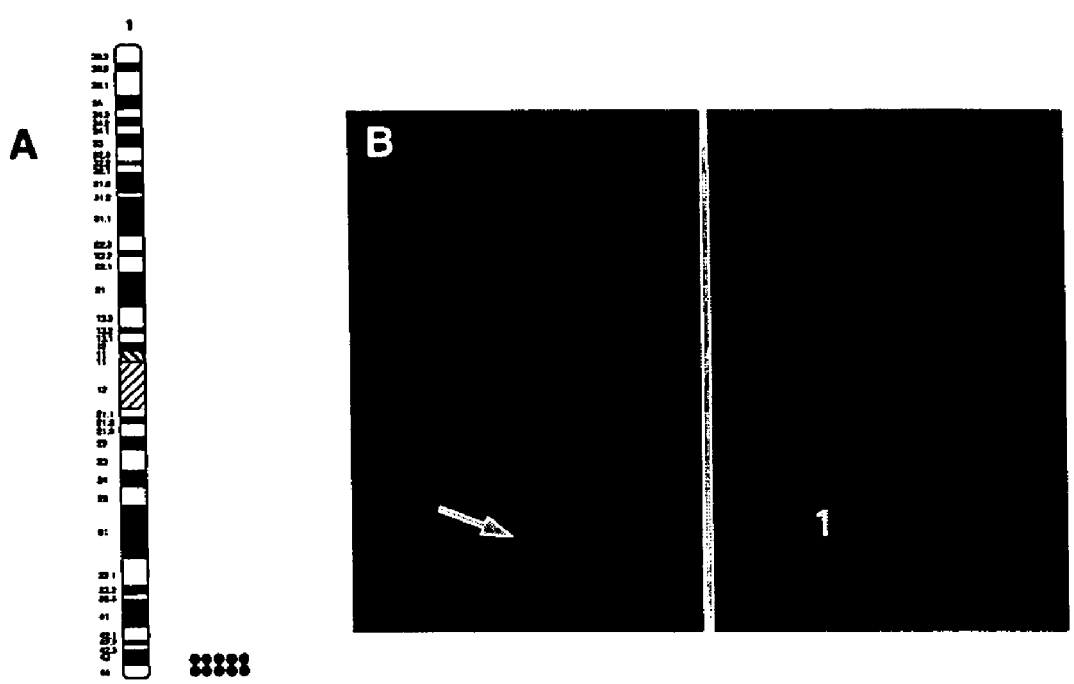
FIG. 5 is an illustration of chromosomal localisation of human Akt-3. (A) Diagram of FISH mapping results of Akt-3. Each dot represents the double FISH signals detected on human chromosome 1, region q43–q44. (B) Example of FISH mapping of Akt-3. The left panel shows the FISH signals on chromosome 1. The right panel shows the same mitotic figure stained with 4',6-diamdino-2-phenylindole to identify chromosome 1.

All primers were obtained from Eurogentec, Seraing, Belgium. Insert-specific sequencing primers (15- and 16-mers) were designed by visual inspection of the DNA sequences. DNA was prepared on Qiagen-tip-20 columns or on Qiaquick spin columns (Qiagen GmbH, Düsseldorf, Germany) and recovered from the spin columns in 30 Fl Tris/EDTA-buffer (10 mM Tris HCl pH 7.5, 1 mM EDTA (sodium salt)). Sequencing reactions were performed using BigDye™ Terminator Cycle Sequencing Ready Reaction kits (Perkin Elmer, ABI Division, Foster City, Calif., USA) and were run on an Applied Biosystems 377 DNA sequencer (Perkin Elmer, ABI Division, Foster City, Calif., USA).

Molecular Cloning of Human Akt-3.

Using the rat RAC-PKγ sequence (Konishi et al, 1995; GenBank acc. No. D49836) as a query sequence, a BLAST (Basic Local Alignment Search Tool; Altschul et al., 1990) search was carried out in the WashU Merck expressed sequence tag (EST) database (Lennon et al., 1996) and in the proprietary LifeSeq™ human EST database (Incyte Pharmaceuticals Inc, Palo Alto, Calif., USA). Several human EST clones with high similarity to the rat RAC-PKγ were identified. One EST sequence (Incyte accession number 2573448) derived from a hippocampal cDNA library, contained part of the coding sequence including the putative methionine start codon (ATG) and part of the 5' untranslated region. The start codon was surrounded by a Kozak consensus sequence for translation start and an in-frame stop codon was present at positions –6 to –3. Based on this 239 bp sequence, oligonucleotide sense primers were synthesised for 3' rapid amplification of cDNA ends (3' RACE) experiments: Akt-3sp1=5'-ACC ATT TCT CCA AGT TGG GGG CTC AG-3' (SEQ ID NO: 4) and Akt-3sp2=5'GGG AGT CAT CAT GAG CGA TGT TAC C-3' (SEQ ID NO: 5). 3'RACE experiments were performed on human fetal brain or human cerebellum Marathon-Ready™ cDNA (Clontech Laboratories, Palo Alto, Calif., USA) according to manufacturer's instructions using Akt-3sp1/race-ap1 as primers in the primary PCR and Akt-3sp2/race-ap2 in the nested PCR. Resulting PCR fragments were cloned and sequenced. This extended the Akt-3 coding sequence by 916 bp, but the novel sequence did not include an in-frame stop codon. A second round of 3' RACE amplification was performed on human brain Marathon Ready™ cDNA using sense primers based on the sequence obtained in the first round (Akt-3sp3=5'CAC TCC AGA ATA TCT GGC ACC AGA GG-3' (SEQ ID NO: 6) and Akt-3sp4=5'CTA TGG CCG AGC AGT AGA CTG GTG G-3') (SEQ ID NO: 7) in combination with race-ap1 and race-ap2, respectively. The sequence obtained included an in-frame stop codon and the 3' untranslated sequence up to the poly(A) tail. Antisense primers were designed based on the 3' untranslated region (Akt-3ap4=5'-TGC CCC TGC TAT GTG TAA GAG CTA GG-3'(SEQ ID NO: 8) and Akt-3ap5=5' AAG AGC TAG GAC TGG TGA TGT CCA GG-3') (SEQ ID NO: 9) and the complete Akt-3 coding sequence was amplified from human hippocampal cDNA using Akt-3sp1/Akt-3ap4 (primary PCR) and Akt-3sp2/Akt-3ap5 (nested PCR) as primers. The resulting 1200 bp PCR fragment was then cloned in the TA-cloning vector pCR2.1 (original TA cloning kit, Invitrogen BV, Leek, The Netherlands) and the inserts of several clones were completely sequenced. One clone containing an insert with the confirmed sequence (hAkt-3/pCR2.1) was used for subsequent subcloning to the mammalian expression vector pcDNA-3 (Invitrogen), yielding construct hAkt-3/pcDNA-3. In order to make a construct coding for a COOH-terminal tagged Akt-3 protein, a fragment of 553 bp was amplified from plasmid Akt-3/pcDNA-3 using an antisense primer incorporating a XhoI restriction site and the sequence coding for a hemagglutinin (HA) tag (YPYDVPDYA) (SEQ ID NO: 13) after amino acid 479 of the Akt-3 sequence. This fragment was recloned into plasmid hAkt-3/pcDNA-3 using BstEII and XhoI restriction sites yielding construct HA-hAkt-3/pcDNA-3.

Constructs and Mutants for *E. coli* Expression of Akt-3.

In order to express the human Akt-3 protein in *E. coli*, the complete Akt-3 coding sequence was amplified from plasmid hAkt-3/pCR2.1 using primers introducing a EcoRI restriction site and a XhoI restriction site at the 5' and 3' ends, respectively. This PCR fragment was cloned as a EcoRI/XhoI fragment in vector pGEX-4T-3 (Amersham Pharmacia Biotech, Uppsala, Sweden) yielding construct hAKT-3(WT)/pGEX-4T-3, and the sequence of the insert was confirmed by sequence analysis.

Mutants of this construct were made using the Quickchange site-directed mutagenesis kit (Stratagene, La Jolla, Calif., USA) according to the manufacturer=s instructions. The T305D mutant (construct hAKT-3(T305D)/pGEX-4T-3) was created by mutating ACA at position 923–925 to GAC, resulting in a Thr$^{305}$ to Asp mutation in the resulting protein. The S472D mutant (construct hAKT-3(S472D)/pGEX-4T-3) was created by changing TC at position 1404–1405 to GA using PCR with a long antisense primer incorporating the change, resulting in a Ser$^{472}$ to Asp mutation in the resulting protein. A double mutant was also constructed by site-directed mutagenesis on hAKT-3 (S472D)/pGEX-4T-3 and contained both these mutations (construct hAKT-3(T305D/S472D)/pGEX-4T-3). The inserts of all resulting constructs were confirmed by complete sequence analysis. The fusion proteins resulting from expression of these constructs in E. coli contain a GST moiety coupled to the NH$_2$-terminus of the human Akt-3 sequence.

Expression in Cos-7 Cells and HEK-293 Cells

Akt-3 was transiently expressed in Cos-7 by calcium phosphate transfection of the cells with the construct HA-hAkt-3/pcDNA-3. The cells were stimulated with 10 ng/ml IGF-1 for 30 minutes, lysed and Akt-3 immunoprecipitated with mAb 12CA5. Akt-3 activity was assessed as described below.

For expression in HEK-293 cells, cells were transfected with pCDNA-3 Akt-3 constructs as described previously (Alessi et al 1996). After stimulation with IGF, the cells were lysed (Alessi et al 1996) and HA-Akt immunoprecipitated with antibody 3F10 (Roche Molecular Biochemicals). Akt activity was assessed in immune complexes by measuring phosphorylation of a peptide substrate (Crosstide) in the presence of 1 µM PKI (PKA inhibitor) and 1 µM GF 109302× (PKC inhibitor) as described.

Expression and Assay of Wild-Type and Mutant Akt-3 in E. coli.

The pGEX expression constructs were transformed into E. coli strain BL21 DE3 and GST-fusion proteins of wild-type and mutated Akt-3 were purified on glutathione sepharose according to the manufacturers instructions (Amersham Pharmacia Biotech, Uppsala, Sweden). The protein eluted from the beads was stored in 50% glycerol at −20° C. Akt activity was assessed by incubating 0.8 Fg of the purified enzyme for 30 minutes at room temperature (unless otherwise indicated) in a buffer containing 10 mM HEPES, 10 mM MgCl$_2$, 1 mM DTT, 0.1 mg/ml histone H2B at pH 7.0, in a total volume of 25 Fl and containing 10 FCi [γ-$^{32}$P]-ATP (6000 Ci/mmol). Initial experiments indicated that the reaction was linear with time for at least 45 minutes. The reaction was stopped by the addition of 25 Fl sample buffer for SDS-PAGE. The results were quantified on a phosphorimager following SDS-PAGE on a 15% (w/v) acrylamide gel.

Chromosomal Mapping Studies

Chromosomal mapping studies were carried out by SeeDNA Biotech Inc, Toronto, Canada using fluorescent in situ hybridisation (FISH) analysis essentially as described (Heng et al., 1992; Heng & Tsui, 1993). Briefly, human lymphocytes were cultured at 37° C. for 68–72 h before treatment with 0.18 mg/ml 5-bromo-2'-deoxyuridine (BrdU) to synchronize the cell cycle in the cell population. The synchronized cells were washed and recultured at 37° C. for 6 h. Cells were harvested and slides were prepared using standard procedures including hypotonic treatment, fixation and air-drying. A cDNA probe for Akt-3 (1.44 kb EcoRI fragment of clone hAkt-3/pcDNA-3) was biotinylated and used for FISH detection. Slides were baked at 55° C. for 1 h, treated with Rnase and denatured in 70% (v/v) formamide in 2× NaCl/Cit (0.3 M NaCl, 0.03 M disodium citrate, pH 7.0) for 2 min at 70EC followed by dehydration in ethanol. Probes were denatured prior to loading on the denatured chromosomal slides. After overnight hybridisation, slides were washed and FISH signals and the 4',6-diamidiono-2-phenylindole banding pattern were recorded separately on photographic film, and the assignment of the FISH mapping data with chromosomal bands was achieved by superimposition of FISH signals with 4,6-diamidino-2-phenylindole banded chromosomes (Heng & Tsui, 1993).

Northern Blot Analysis.

Northern blots containing 2 Fg of poly(A)-rich RNA derived from different human tissues (Clontech Laboratories, Palo Alto, Calif., USA) were hybridised according to the manufacturer's instructions with a α-$^{32}$P-dCTP random-priming labelled (HighPrime kit, Boehringer Mannheim) 454 bp NotI-XbaI Akt-3 fragment (nucleotides 1404 to 1857) corresponding to part of the 3' untranslated sequence.

Reverse Transcription (RT)-PCR Analysis

Oligonucleotide primers were designed for the specific PCR amplification of a fragment from Akt-3. These primers were Akt-3sp2=5'-GGG AGT CAT CAT GAG CGA TGT TAC C-3' (SEQ ID NO: 5) (sense primer) and Akt-3ap1=5'-GGG TTG TAG AGG CAT CCA TCT CTT CC-3' (SEQ ID NO: 11) (antisense primer), yielding a 425 bp product. PCR amplifications for human glyceraldehyde-3-phosphate dehydrogenase (G3PDH) were performed on the same cDNA samples as positive controls using G3PDH primers 5'-TGA AGG TCG GAG TCA ACG GAT TTG GT-3'(SEQ ID NO: 10) (sense primer) and 5'-CAT GTG GGC CAT GAG GTC CAC CAC-3' (SEQ ID NO: 14) (antisense primer), yielding a 1000 bp fragment. These primers were used for PCR amplifications on Multiple Tissue cDNA panels (Clontech Laboratories) and on cDNA prepared from tumor cell lines. For the preparation of tumor cell cDNA, cells were homogenised and total RNA prepared using the RNeasy Mini kit (Qiagen GmbH, Hilden, Germany) according to manufacturer's instructions. 1 Fg of total RNA was reverse transcribed using oligo(dT)$_{15}$ as a primer and 50 U of Expand™ Reverse Transcriptase (Boehringer Mannheim, Mannheim, Germany) according to the manufacturer's instructions. PCR reactions with Akt-3-specific or G3PDH-specific primers were then performed on 1 Fl of cDNA. Images of the ethidium bromide stained gels were obtained using the Eagle Eye II Video system (Stratagene, La Jolla, Calif., USA) and PCR bands analysed using the EagleSight software.

Assays to Identify Agents that Modulate the Activity of Akt-3

To identify agents that modulate the activity of Akt-3, SPA (scintillation proximity assay) and filter assays for Akt-3 activity were developed.

Figure 7:
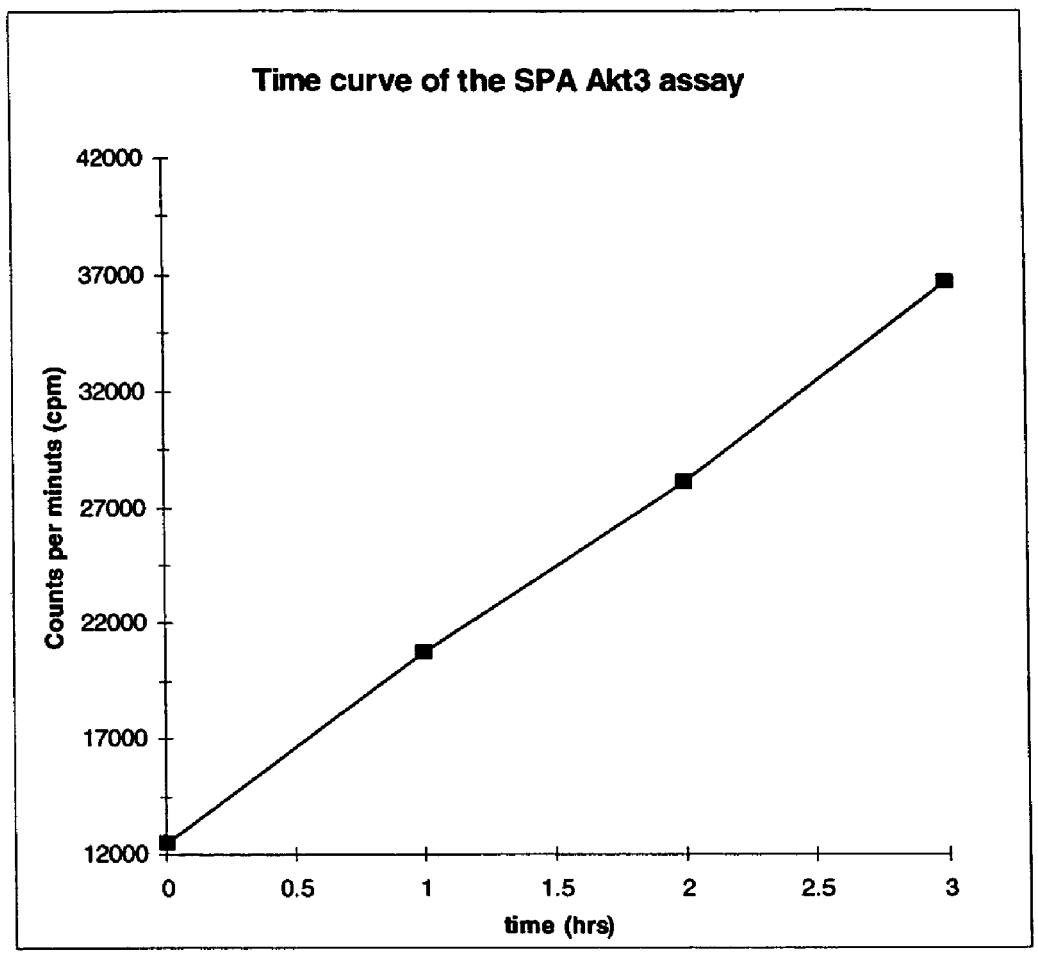
FIG. 7 is an illustration of the results obtained by scintillation counting in a scintillation proximity assay to identify agents that modulate the activity of Akt-3 activity.

SPA assays were performed at 25° C. for 3 hrs in the presence of 25 mM Hepes, pH 7.0, containing 15 mM MgCl$_2$, 1 mM DTT. Each assay was performed in a 100 Fl reaction volume containing 111 nM GST-AKT-3 (diluted in 25 mM Hepes, pH 7.0, containing 15 mM MgCl$_2$, 1 mM DTT), 0.75 FM Biotinylated Histone H2B, 2 nM [γ-$^{33}$P]-ATP and any agents under test. The reaction was terminated by addition of 100 Fl Stop mix (50 FM ATP, 5 mM EDTA, 0.1% BSA, 0.1% Triton X-100 and 7.5 mg/ml Streptavidin coated PVT SPA beads). After allowing the beads to settle for 30 minutes, the assay mixture was counted in a microtiterplate scintillation counter. The results are illustrated in FIG. 7.

Figure 8:
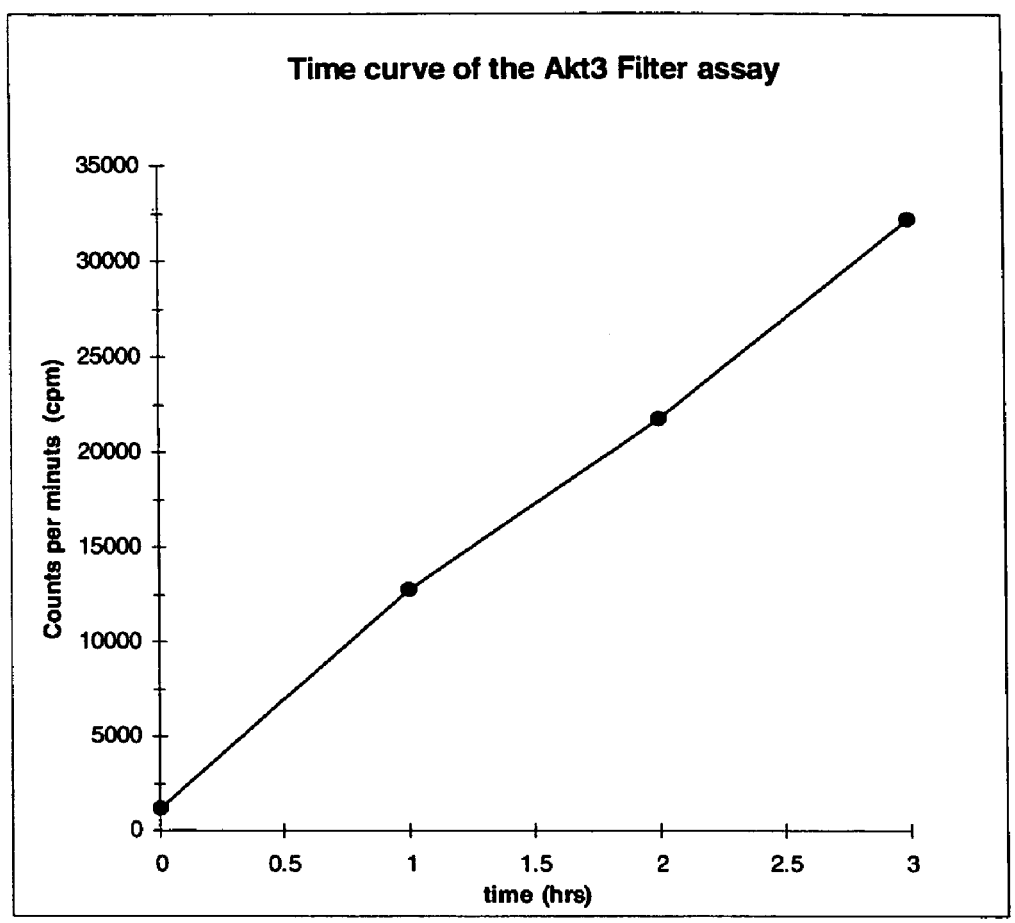
FIG. 8 is an illustration of the results obtained from an Akt-3 filter assay to identify agents that modulate activity of Akt-3.

AKT3 filter assays were performed at 25° C. for 3 hrs in the presence of 25 mM Hepes, pH7.0, containing 15 mM MgCl$_2$, 1 mM DTT. Each assay was performed in a 100 Fl reaction volume containing 111 nM GST-AKT-3 (diluted in 25 mM Hepes, pH7.0, containing 15 mM MgCl$_2$, 1 mM DTT), 2.5 FM Histone H2B, 2 nM [γ-$^{33}$P]-ATP and any agents under test. The reaction was terminated by addition of 100 Fl 75 mM H$_3$PO$_4$. 90 Fl of the assay mixture was filtered through Phosphocellulose cation exchange paper. After five times washing with 75 FM H$_3$PO$_4$, the filterpaper was counted in a microtiterplate scintillation counter. The results are illustrated in FIG. 8.

Results

Molecular Cloning of Human Akt-3.

Similarity searching of the LifeSeq™ and EMBL databases using the rat Akt-3 sequence as a query sequence yielded several human EST sequences which encoded part of the human homologue of rat Akt-3. Using the DNA sequence information in the databases, we were able in subsequent 3' RACE experiments to deduce the complete cDNA sequence for the human Akt-3 (FIG. 1) (SEQ ID NO:1, coding DNA is provided as SEQ ID NO:2). The obtained cDNA sequence encoded a protein of 479 amino acid residues (SEQ ID NO:3) with a calculated molecular mass of 55770 Da. The first 451 amino acids of the human Akt-3 protein contain only two differences to the corresponding rat sequence (Konishi et al., 1995)—Asp (rat) to Gly (human) at position 10 and Pro (rat) to Ala (human) at position 396 and encode a pleckstrin homology domain, a kinase domain and a COOH-terminal "tail". The two amino acid residues that are presumed to be phosphorylated upon activation of Akt-3 (Thr$^{305}$ and Ser$^{472}$) are in bold and marked with an asterisk. The COOH-terminal part of the human Akt-3 protein that differs with the rat homologue extends from amino acid 452 through amino acid 479. The predicted Akt-3 (FIG. 2) protein shows significant similarity with Akt-1 (Jones et al, 1991; 83.6% identity; 87.8% similarity) and with Akt-2 (Cheng et al., 1992; 78% identity; 84.3% similarity). The COOH-terminal 'tail' has been observed in both human and rat Akt-1 and Akt-2 proteins, but it is apparently truncated in the only other reported Akt-3 sequence (rat Akt-3, Konishi et al., 1995; accession number D49836). 3'RACE experiments performed on human cDNAs derived from different tissues did not yield evidence for the existence of a shorter form of Akt-3 that would be analogous to the rat Akt-3 (data not shown). The tail in human Akt-3 comprises 28 amino acid residues (YDEDG-MDCMDNERRPHFPQFSYSASGRE) (SEQ ID NO: 12) that replace 3 amino acid residues in the rat sequence (CPL). The tail in human Akt-3 contains a serine residue at position 472 (shown in bold) that corresponds to Ser$^{473}$ in Akt-1 or Ser$^{474}$ in Akt-2. Phosphorylation of Ser$^{473}$ and Ser$^{474}$ has previously been implicated in the activation of Akt-1 and Akt-2, respectively (Alessi et al., 1996; Meier et al., 1997). Thr$^{308}$ (in the kinase domain) has also been implicated in the activation of Akt-1 and this residue is also conserved in human Akt-3 (Thr$^{305}$).

Characterisation of Akt-3 Activity.

To characterise the enzymatic activity of Akt-3, we expressed and purified the recombinant enzyme as a GST fusion protein. Analysis of the purified product by SDS-PAGE indicated the protein was apparently >90% pure. The purified enzyme was able to phosphorylate histone H2B (FIG. 3), and no phosphorylation was observed using recombinant GST alone. Previously, the enzymatic activity of Akt-1 has been shown to be increased by phosphorylation of Thr$^{308}$ and Ser$^{473}$, and mutation of both these residues to Asp (to mimic phosphorylation) synergistically activates Akt-1 (Alessi et al., 1996). To investigate whether Akt-3 is similarly regulated, GST-fusion proteins in which either Thr$^{305}$ or Ser$^{472}$ (corresponding to Thr$^{308}$ and Ser$^{473}$ in Akt-1) or both Thr$^{305}$ and Ser$^{472}$ had been mutated to Asp were expressed and assayed in comparison to the wild-type enzyme. Mutation of Thr$^{305}$ to Asp ("T305D") resulted in a 2.0-fold increase in the initial rate of phosphorylation of histone H2B, whereas mutation of Ser$^{472}$ to Asp(S472D") increased the initial rate only 1.4 fold (FIG. 3A). When both Thr$^{305}$ and Ser$^{472}$ ("T305D,S472D) were mutated to Asp, a 3.2-fold increase in the initial phosphorylation rate was observed.

To confirm that extracellular stimuli can activate Akt-3 in mammalian cells, Cos-7 cells were transfected with a cDNA encoding Akt-3 fused to a HA tag. Akt-3 activity in HA immunoprecipitates was increased 1.5 and 1.9 fold (n=2) following stimulation with IGF-1 (10 ng/ml).

To further confirm that extracellular stimuli can activate Akt-3 in mammalian cells, HEK-293 cells were transfected with a cDNA encoding Akt-3 fused to a HA epitope tag. Upon treatment with IGF, Akt-3 activity in anti-HA immunoprecipitates (FIG. 3B) was increased almost 60-fold above that in untransfected cells (FIG. 3C). Akt variants in which Thr$^{305}$ and Ser$^{472}$ were mutated to alanine were refractory to activation by IGF. Consistent with this, Western blotting with a Ser$^{472}$ phosphospecific antibody of HA immunoprecipitates from cells stimulated with IGF demonstrated that Ser$^{472}$ was phosphorylated following stimulation with IGF (FIG. 3B). In addition, activation of Akt-3 was inhibited by prior treatment with CY29 4002 (100 FM, 94% inhibition), data not shown).

To characterise human Akt-3 further, we investigated the ability of a range of Ser/Thr kinase inhibitors to inhibit Akt-3. These included Go 6976, GF-109203× (both protein kinase C (PKC) inhibitors); H-85, H-88, H-89 and KT5720 (protein kinase A (PKA) inhibitors), KN-62 (Ca$^{+2}$/Calmodulin dependent kinase inhibitor) and PD 98059 (MEK inhibitor). When tested at a concentration of 10 FM these compounds had no significant effect on the activity of the T305D,S472D variant of Akt-3. However, the broad spectrum kinase inhibitor staurosporine (IC$_{50}$=2.0±0.3 FM) and the PKC inhibitor Ro 31-8220 (IC$_{50}$=3.2±1.0 FM) inhibited the T305D,S472D variant of Akt-3 (FIG. 4).

Chromosomal Localisation of Akt-3.

The complete coding sequence of Akt-3 was used as a probe for FISH analysis. Under the conditions used, the hybridisation efficiency was approximately 75% for this probe (among 100 checked mitotic figures, 75 of them showed signals on one pair of the chromosomes). Since the DAPI-banding was used to identify the specific chromosome, the assignment between the signal from the probe and the long arm of chromosome 1 was obtained. The detailed position was further determined in the diagram based upon the summary from 10 photographs (FIG. 5A). There was no additional locus picked by FISH detection under the conditions used, therefore, it was concluded that Akt-3 is located at human chromosome 1, region q43–q44. An example of the mapping results is presented in FIG. 5B.

Tissue Distribution of Akt-3 mRNA.

Figure 6A:
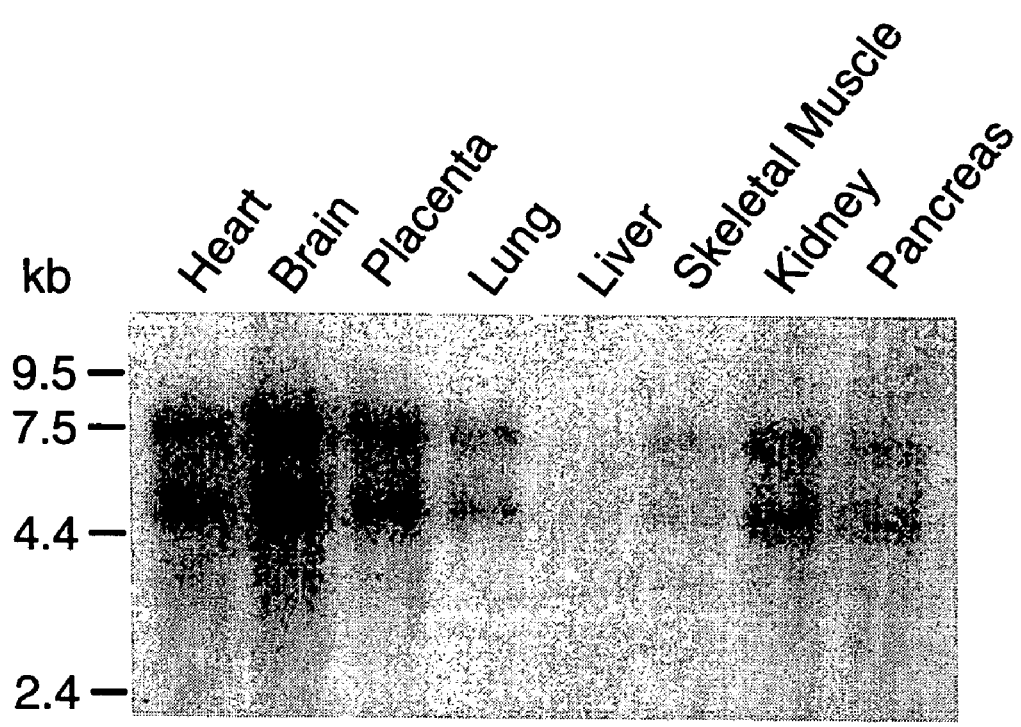
FIG. 6 is an illustration of expression of Akt-3 in different human tissues. (A) Northern blot analysis of tissue expression of Akt-3. The expression of hAkt-3 mRNA in different human tissues was assessed using a probe corresponding to the 3' untranslated region of hAkt-3 to analyse a blot of human polyA$^+$ RNA (AMultiple Tissue Northern≙). Human β-actin was used as a control to confirm equal loading of the lanes (data not shown). (B) and (C) RT-PCR analysis of tissue expression of Akt-3. RT-PCR analyses were performed on cDNA from different human tissues (B) and from different tumor cell lines (C) using primers specific for human Akt-3 or G3PDH (control) for the indicated number of PCR cycles. Bands of the expected size (425 bp for Akt-3 and 1 kb for G3PDH) are visible on the gels. The images from the ethidium bromide stained 1.2% agarose gels were inverted for clarity using the EagleSight software (Stratagene). The results from similar PCR reactions performed for 25, 30 or 35 cycles are not shown but indicated that the results from this figure are in the linear range of amplification. Caco-2=colorectal adenocarcinoma; T-84=colorectal carcinoma; MCF-7=breast adenocarcinoma; T-47D=breast ductal gland carcinoma; HT1080=bone fibrosarcoma; SaOS-2=osteosarcoma; SK-N-MC=neuroblastoma; HepG2=hepatoblastoma; JURKAT=T-cell leukemia.

Northern blot analysis was performed on mRNA derived from different human tissues. Akt-3 mRNA was detected as two transcripts of approximately 4.5 kb and 7.5 kb, showing similar patterns of expression (FIG. 6A). Akt-3 mRNA was expressed in a range of tissues, most prominently in brain. Similarly, rat Akt-3 was detected as multiple transcripts most highly expressed in brain (Konishi et al., 1995). The weakest expression of Akt-3 was observed in two insulin-responsive tissues, skeletal muscle and liver. Akt-3 was also expressed in a number of cancer cell lines including SW480 colorectal adenocarcinoma, A549 lung carcinoma and G361 Melanoma (data not shown).

Figure 6B:
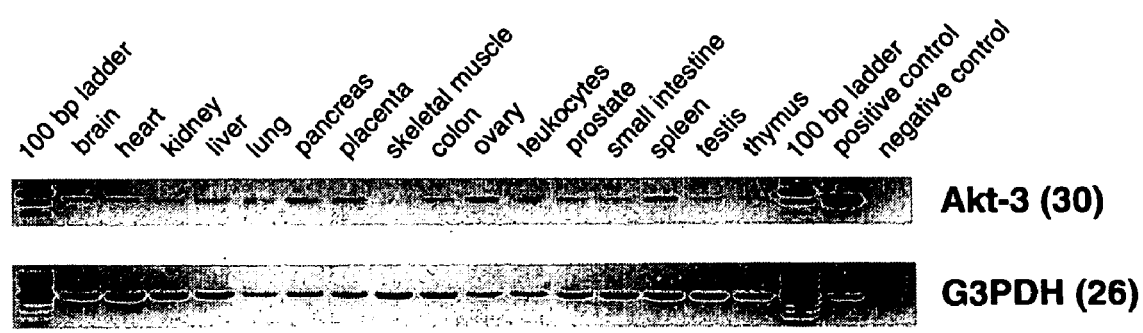
Figure 6C:
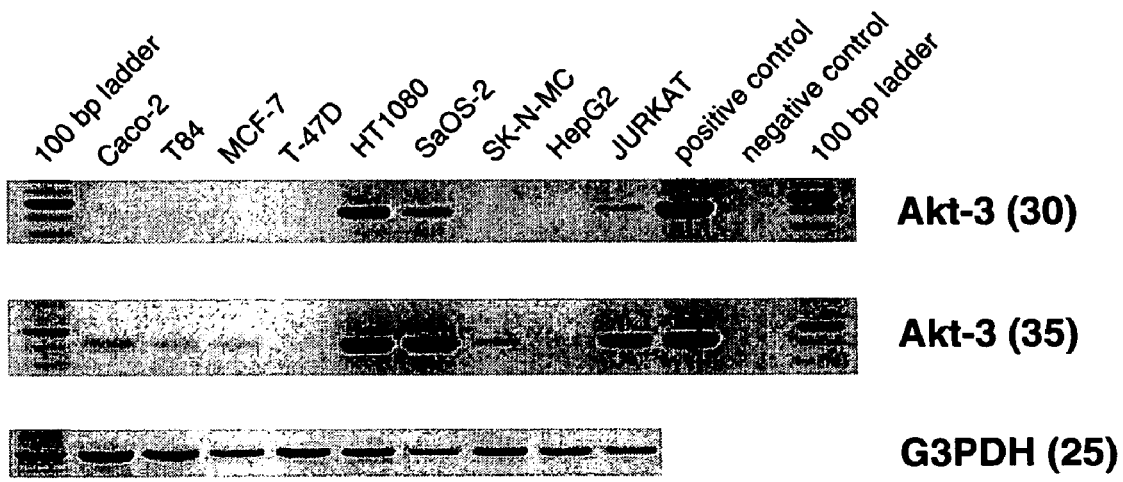

To confirm the Northern blot analysis, PCR reactions were performed with Akt-3 specific and G3PDH-specific (internal control) primers on cDNAs derived from different human tissues (FIG. 6B). The Akt-3 message was present in every tissue tested, since a specific 425 bp fragment was amplified in every cDNA after 30 cycles of PCR. Akt-3 mRNA expression was high in placenta, ovary and spleen. Moderate expression was seen in brain, heart, kidney, colon, prostate, small intestine and testis. Lowest expression was in liver, lung, pancreas, skeletal muscle, peripheral blood leukocytes and thymus. In tumor cell lines (FIG. 6C), Akt-3 mRNA expression was relatively high in HT-1080 bone fibrosarcoma cells, in SaOS-2 osteosarcoma and in JURKAT T-cell leukemia cells (Akt-3 band detectable after 30 cycles of PCR). Caco-2 colorectal adenocarcinoma, T84 colorectal carcinoma, MCF-7 breast adenocarcinoma and SK-N-MC neuroblastoma cells show Akt-3 mRNA expression after 35 cycles of PCR. In T-47D breast ductal gland carcinoma and HepG2 hepatoblastoma, expression of Akt-3 mRNA is very low or absent (no signal detectable after 35 cycles of PCR).

Akt-1 and Akt-2 have been identified in several species. Human (Jones et al., 1991; Coffer et al 1991), mouse (Bellacosa et al., 1993) and bovine (Coffer & Woodgett, 1991) Akt-1 clones have been reported, whereas human (Cheng et al., 1992) mouse (Altomare et al., 1995) and rat (Konishi et al., 1994) clones of Akt-2 have been identified. However, Akt-3 has only been previously identified in rat (Konishi et al, 1995). The present inventors have identified the human isoform of Akt-3. Although human Akt-3 shows considerable similarity to human Akt-1 and Akt-2, the discovery of human Akt-3 is particularly significant because the cDNA sequence encodes a COOH-terminal Atail≅ which includes a phosphorylation site implicated in the activation of Akt-1 and Akt-2 (Alessi et al., 1996; Meier et al., 1997). This tail is absent from the predicted rat amino acid sequence. Human Akt-3 appears to be activated by phosphorylation in a similar fashion as Akt-1 and Akt-2. However, its expression profile suggests that the principal function of this enzyme is not in regulating responses to insulin.

The sequence which has been identified represents the human homologue of Akt-3. This assignment is based on the >99% identity between the rat and human Akt-3 protein sequences. With the exception of the COOH-terminal tail seen in human Akt-3, there are only 2 amino acid differences ($Gly^{10}$ and $Ala^{396}$ in human Akt-3) between the rat and human Akt-3 proteins. Alignment of all the previously described Akt sequences demonstrates that $Gly^{10}$ and $Ala^{396}$ in the human protein correspond to Gly and Ala residues respectively in the Akt-1 and Akt-2 sequences identified from other species. Further evidence that we have identified the Akt-3 isoform comes from the presence of isotype-specific sequences represented by human Akt-3 residues 47–49 (LPY), 118–122 of SEQ ID NO: 3 (NCSPT) and 139–141 (HHK). For each isotype, these sequences are conserved between species, but differ between the isotypes.

The human Akt-3 cDNA sequence was predicted to encode a $NH_2$-terminal pleckstrin homology (PH) domain (Musacchio et al., 1993) and a COOH-terminal kinase domain. A striking difference between the human and rat Akt-3 protein sequence (Konishi, et al., 1995) is the presence of a COOH-terminal Atail≅ comprising 74 residues after the kinase domain. The last 28 amino acid residues in human Akt-3 are absent from the rat Akt-3 sequence. We were unable to identify human cDNA sequences that encoded a similar truncation, despite conducting RACE experiments using cDNA from several different human tissues. The region in human Akt-3 that is absent from rat Akt-3 encompasses a stretch of 10 residues (residues 467–476 in human Akt-3) which are identical to the corresponding region of human Akt-1 and Akt-2. This suggests that the tail observed in human Akt-3 is authentic. The significance of the difference observed in the rat Akt-3 tail region remains to be investigated. However, the human Akt-3 COOH-terminal sequence includes $Ser^{472}$, which corresponds to $Ser^{473}$ in Akt-1. Phosphorylation of $Ser^{473}$ has been shown to lead to a 5-fold increase in the activity of Akt-1, whereas a 20–25 fold increase of Akt-1 activity is observed if both $Ser^{473}$ and $Thr^{308}$ are phosphorylated (Alessi et al., 1996). Thus, our observation that $Ser^{472}$ is present in human Akt-3 is significant, because it suggests that human Akt-3 is potentially regulated in a manner similar to Akt-1 and Akt-2. Whether rat Akt-3 is regulated in a different fashion remains to be resolved.

The kinase and PH domains in Akt-3 show homology to the consensus PH and kinase domain sequences (Musacchio et al., 1993; Hanks & Hunter 1995). The PH domain of human Akt-3 is 77% and 86% identical to the PH domains in Akt-1 and Akt-2, respectively, while the kinase domain of Akt-3 is 88% and 87% identical to the kinase domain of Akt-1 and Akt-2, respectively. The high conservation of the PH domain may indicate an Akt-specific function, because PH domains are often highly divergent (Musacchio et al, 1993). Apart from binding phosphoinositides, the PH domain of Akt has been shown to mediate interactions between Akt and PKC (Konishi, et al., 1995) as well as directing the formation of multimeric Akt complexes (Datta et al, 1995). In contrast, the region between the PH domain and the kinase domain is poorly conserved between the human Akt-1, Akt-2 and Akt-3 sequences, and this region is also important for mediating the formation of multimeric Akt complexes (Datta et al, 1995). This raises an interesting issue—whether the sequence $NH_2$-terminal to the kinase domain of Akt-3 mediates the interaction with binding partners that are unique to Akt-3 or that bind to multiple Akt isoforms.

To verify that the predicted kinase domain was catalytically active, we expressed Akt-3 as a GST fusion protein in *E. coli*. The purified protein was able to phosphorylate an exogenous substrate, whereas no catalytic activity was observed using GST in place of GST-Akt-3. To confirm that Akt-3 is indeed regulated in a manner akin to Akt-1 and Akt-2, we mutated $Thr^{305}$ and $Ser^{473}$, either separately or jointly, to Asp. This strategy has previously been shown to faithfully mimic the effect of phosphorylation of these residues in Akt-1 (Alessi et al., 1996). Mutation of either of these residues resulted in increased activity, although the increase was less than that observed with Akt-1 (Alessi et al., 1996). Additionally, we did not observe a synergistic activation of Akt-3 by mutation of both $Thr^{305}$ and $Ser^{473}$. In contrast, when both the corresponding residues were simultaneously mutated to Asp in Akt-1, synergistic activation was observed (Alessi et al, 1996). The apparent quantitative differences between Akt-1 and Akt-3 may reflect true differences in the regulation of these two isoforms, or it may be due to other factors such as the different expression system used. In the present study Akt-3 was expressed as a GST fusion protein in E. coli, whereas Akt-1 activity was studied using an HA-tagged protein expressed in COS cells. Nevertheless, our results demonstrate that Akt-3 is qualitatively regulated in a fashion similar to Akt-1. Previous work has also shown that activation of Akt is dependent upon PI 3-kinase to generate 3-phosphoinositides that bind the PH domain of Akt, promote translocation of Akt to the plasma membrane and facilitate the phosphorylation of Akt by upstream kinases (reviewed in Alessi & Cohen, 1998; Coffer et al., 1998). Our observation that the T305D/S472D mutant of Akt-3 is more active than the wild type enzyme (FIG. 3), when measured in the absence of 3-phosphoinositides, suggests that after phosphorylation Akt-3 becomes (at least partially) independent of phosphoinositide binding.

The structure of the catalytic domain of Akt is closely related to protein kinase A and protein kinase C. Indeed, a BLAST search of the SwissProt data base revealed that the most closely related kinases (other than the different Akt isoforms) include several protein kinase C isozymes. This prompted us to investigate whether existing inhibitors of PKA or PKC, as well as other serine/threonine kinase inhibitors, could be used as inhibitors of Akt-3. Of the compounds tested, only staurosporine and the structurally related compound Ro 31-8220 both potently inhibited Akt-3. Staurosporine is a non-selective kinase inhibitor, whereas Ro 31-8220 is a more selective PKC inhibitor (Davis, et al., 1992). Although Ro 31-8220 is an approximately 100-fold more potent ($IC_{50}$.10 nM; Davis, et al., 1992) inhibitor of PKC than of Akt-3, this observation cautions that experiments using high concentrations of Ro 31-8820 may affect Akt-3. In contrast to staurosporine and Ro 31-8220, two other PKC inhibitors and three other PKA inhibitors did not inhibit Akt-3. This suggests that although Akt-3 is closely related in sequence to PKC, it may be possible to find selective inhibitors of Akt.

The observation that Akt-3 is activated by IGF-1 suggests that Akt-3 may play a role in regulating cell survival. Akt-3 potentially may suppress apoptosis in tumor cells. One concern in using Akt as a target for drug development in cancer is that Akt plays a role in insulin signalling (reviewed in Sheperd et al, 1998). Thus, inhibitors of Akt may induce symptoms observed in patients with diabetes. One solution that has been proposed is to develop selective inhibitors of Akt-2 (Walker et al, 1998). This is based in part on the observation that Akt-1 is strongly activated by insulin in rat hepatocytes and skeletal muscle, whereas Akt-2 is only weakly activated by insulin in these tissues. However, rat Akt-3 appears to be even more weakly activated by insulin in these tissues (Walker et al, 1998), and in this study we have shown that Akt-3 mRNA is expressed only at low levels in human liver and skeletal muscle, which are insulin responsive tissues. This suggests that selective inhibitors of Akt-3 could have even less potential to cause symptoms similar to those seen in patients with diabetes than do inhibitors of Akt-2. The localisation of human Akt-3 to human chromosome 1q43–44 is also interesting, as patients with haematological cancers have been reported with chromosomal abnormalities in this region (Mitelman et al, 1997). Although the significance of the latter observation is debatable, as chromosomal abnormalities at numerous loci have been observed in patients with haematological cancers, the results presented here indicate that Akt-3 may prove to be an important target for the development of novel therapeutics for the treatment of cancer.

Sequence Listing
1. Sequence ID No. 1 corresponds to the nucleotide sequence of Akt-3 illustrated in FIG. 1.
2. Sequence ID No. 2 corresponds to from nucleotide position 11 to 1447 of the nucleic acid sequence of Akt-3 illustrated in FIG. 1.
3. Sequence ID No. 3 corresponds to the amino acid sequence of Akt-3 illustrated in FIGS. 1 and 2.

REFERENCES

Ahmed, N. N, Grimes, H. L., Bellacosa, A., Chan, T. O., Tsichlis (1997) Transduction of interleukin-2 antiapoptotic and proliferative signals via Akt protein kinase. *Proc. Natl. Acad Sci USA* 94, 3627–3632.

Alessi, D. R. & Cohen, P. (1998) Mechanism of activation and function of protein kinase B. *Current Opinion Gen. Dev.* 8, 55–62.

Alessi, D. R., Andjelkovic, M., Caudwell, F. B., Cron, P. Morrice, N., Cohen, P. & Hemmings, B. (1996) Mechanism of activation of protein kinase B by insulin and IGF1. *EMBO J.* 15, 6541–6551.

Alessi, D. R., Deak, M., Casamayor, A., Caudwell, F. B., Morrice, N., Norma, D. G., Gaffney, P., Reese, C. B., MacDougall, C. N., Harbison, D., Ashworth, A. & Bownes, M. (1997) 3-phosphoinositide-dependent protein kinase-1 (PDK-1): structural and functional homology with the *Drosophila* DSTP61 kinase. *Curr. Biol.* 7:776–789.

Altomare, D. A., Guo, K, Cheng, J. Q., Sonoda, G., Walsh, K. & Testa, J. R., (1995) Cloning, chromosomal localisation and expression analysis of the mouse Akt2 oncogene. *Oncogene* 11, 1055–1060.

Altschul, S. F., Gish, W., Miller, W., Myers, E. W. & Lipman, D. J. (1990). Basic local alignment search tool, *J. Mol. Biol.* 215, 403–410.

Bellacosa, A., Franke, T. F., Gonzalez-Portal, M. E., Detta, K., Taguchi, T., Gardner, J., Cheng, J. Q., Testa, J. R. & Tsichlis, P. N. (1993) structure, expression and chromosomal mapping of c-akt: relationship to v-akt and its implications. *Oncogene* 8, 745–754.

Bellacosa, A., De Feo, D., Godwin, A. K., Bell, D. W., Cheng, J. Q., Altomare, D. A., Wan, M., Dubeau, L., Scambia, G., Masciullo, V., Ferrandina, G., Benedetti Panicini, P., Mancuso, S., Neri, G. & Testa, J. R. (1995) Molecular alterations of the Akt2 oncogene in ovarian and breast cancer, *Int. J. Cancer* 64, 280–285.

Cheng, J. Q., Godwin, A. K., Bellacosa, A., Taguchi, T., Franke, T. F., Hamilton, T. C., Tsichlis, P. N. & Testa, J. R. (1992) AKT2, a putative oncogene encoding a member of a subfamily of protein-serine/threonine kinases, is amplified in human ovarian carcinomas. *Proc. Natl. Acad. Sci. USA* 89, 9267–9271.

Coffer, P. J. & Woodgett, J. R. (1991) Molecular cloning and characterisation of a novel putative protein-serine kinase related to the cAMP-dependent and protein kinase C. families. *Eur. J. Biochem.* 201, 475–481.

Coffer, P. J., Jin, J. & Woodgett, J. R. (1998) Protein kinase B (c-Akt)—A multifunctional mediator of phosphatidylinositol 3-kinase activation. *Biochem J.* 335:1–13.

Cohen, P., Alessi, D. R. & Cross, D. A. E. (1997) PDK1, the missing link in insulin signal transduction? *FEBS Lett.* 410, 3–10.

Crowder, R. J. & Freeman, R. S. (1998) Phosphatidylinositol 3-kinase and Akt protein kinase are necessary and sufficient for the survival of nerve growth factor-dependent sympathetic neurons, *J. Neurosci.* 18, 2933–2943.

Datta, S. R., Dudek, H., Tao, X., Masters, S., Fu, H. A., Gotoh, Y. & Greenberg, M. E. (1997) Akt Phosphorylation of BAD couples survival signals to the cell-intrinsic death machinery. *Cell.* 91, 231–241.

Davis, P. D., Elliot L. H., Harris, W., Hill, C. H., Hurst, S. A., Keech, E., Kumar, M. K., Lawton, G., Nixon, J. S. & Wilkinson, W. E. (1992) Inhibitors of protein kinase C. 2. Substituted bisindoylmaleimides with improved potency and selectively. *J. Med. Chem.* 35, 994–1001.

del Peso, L., Gonzalez-Garcia, M., Page, C., Herrera, R., Nunez, G., (1997) Interleukin-3-induced phosphorylation of BAD through the protein kinase Akt. *Science* 278, 687–689.

Delcommenne, M., Tan, C., Gray, V., Rue, L. Woodgett, J. & Dedhar, S. (1998) Phosphoinositide-3-OH kinase-dependent regulation of glycogen synthase kinase 3 and protein kinase B/AKT by the intergrin-linked kinase. *Proc. Natl. Acad. Sci. USA* 95, 11211–11216.

Dudek, H., Datta, S. R., Franke, T. F., Bimbarun, M. J., Yao, R., Cooper, G. M., Segal, R. A., Kaplan, D. R. & Greenberg, M. E. (1997) Regulation of neuronal survival by the serine-threonine protein kinase Akt. *Science* 275, 661–665.

Eves, E. M., Xiong, W., Bellacosa, A., Kennedy, S. G., Tsichlis, P. N., Rosner, M. R. & Hay, N. (1998) Akt, a target of phosphatidylinositol 3-kinase, inhibits apoptosis in a differentiating neuronal cell line. *Mol. Cell. Biol.* 18, 2143–2152.

Frisch S. M. & Francis, H. (1994) Disruption of epithelial cell-matrix interactions induces apoptosis, *J. Cell. Biol.* 124, 619–626.

Frisch, S. M. & Ruoslahti, E. (1997) Integrins and Anoikis. *Curr. Op. Cell. Biol.* 9, 701–706.

Hanks, S. K. & Hunter, T. (1995) The eukaryotic protein kinase superfamily: kinase (catalytic) domain structure and classification *FASEB J.* 9, 576–596.

Hemmings, B. A. (1997) Akt signaling: linking membrane events to life and death decisions. *Science* 275, 628–630.

Heng, H. H. Q. & Tsui, L.-C. (1993) Modes of DAPI banding and simultaneous in situ hybridization. *Chromosoma* 102, 325–332.

Heng, H. H. Q., Squire, J. & Tsui, L.-C. (1992) High resolution mapping of mammalian genes by in situ hybridization to free chromatin. *Proc. Natl. Acad. Sci. USA* 89, 9509–9513.

Jones, P. F., Jakubowicz, T., Pitossi, F. J., Maurer, F. & Hemmings, B. A. (1991) Molecular cloning and identification of a serine/threonine protein kinase of the second-messanger subfamily. *Proc. Natl. Acad. Sci. USA* 88, 4171–4175.

Kauffmann-Zeh, A., Rodriquez-Viciana P., Ulrich, E., Gilbert, C., Coffer, P., Downward, J. & Evan, G. (1997) Suppression of c-Myc-induced apoptosis by ras signalling through PI(3)K and PKB. *Nature* 385, 544–548.

Kennedy, S. G., Wagner, A. J., Conen, S. D., Jordan, J., Bellacosa, A., Tsichlis, A. N. & Hay, N. (1997) The PI 3-kinase/Akt signalling pathway delivers an anti-apoptotic signal. *Genes & Development* 11, 701–713.

Khwaja, A., Rodriquez-Viciana, P. Wennstrom, S., Warne, P. H. & Downward, J. (1997) Matrix adhesion and ras transformation both activate a phosphoinositide 3-OH kinase and protein kinase B/Akt cellular survival pathway. *EMBO J.* 16, 2783–2793.

Konishi, H., Shinomuara, T., Kuroda, S., Ono, Y. & Kikkawa, U. (1994) Molecular Cloning of rat RAC protein kinase α and β and their association with protein kinase Cζ. *Biochem. Biophys. Res. Commn* 205, 817–825.

Konishi, H., Kuroda, S., Tanaka, M., Matsuzaki, H., Ono, Y., Kameyama, K., Haga, T. & Kikkawa, U. (1995) Molecular cloning and characterisation of a new member of the RAC protein kinase family: association of the pleckstrin homology domain of three types of RAC protein kinase with protein kinase C subspecies *and* βγ subunits of G proteins. *Biochem. Biophys. Res. Commun.* 216, 526–534.

Kulik, G., Klippel, A. & Weber, M. J. (1997) Anti-apoptotic signalling by the insulin-like growth factor receptor, phosphatidylinositol-3 kinase and Akt. *Mol. Cell. Biol.* 17, 1595–1606.

Lennon, G., Auffray, C., Polymeropoulos, M. & Soares, M. B. (1996) The I.M.A.G.E. Consortium: an integrated molecular analysis of genomes and their expression. *Genomics* 33, 151–152.

Marte, B. M. & Downward, J. (1997) PKB/Akt: connecting phosphoinositide 3-kinase to cell survival and beyond. *Trends Biochem. Sci.* 22, 355–358.

Marte, B. M., Rodriquez-Viciana, P., Wennstrom, S., Warne, P. H. & Downward, J. (1997) R-Ras can activate the phosphoinositide 3-kinase but not the MAP kinase arm of the Ras effector pathways (1997) *Curr. Biol.* 7, 63–70.

Meier, R., Alessi, D. R., Cron, P., Andjelkovic, M. & Hemmings, B. A. (1997) Mitogenic activation, phosphorylation and nuclear translocation of protein kinase β. *J. Biol. Chem.* 272, 30491–30497.

Meredith J. E. Jr., Fazeli, B. & Schwartz, M. A. (1993) The extracellular matrix as a survival factor, *Mol. Cell Biol* 4, 953–961.

Mitelman, F., Mertens F. & Johansson, B., (1997) A breakpoint map of recurrent chromosomal rearrangements in human neoplasia, *Nature Genetics* 15, 417–474.

Musacchio, A., Gibson, T., Rice, P., Thompson, J. & Saraste, M. (1993) The PH domain: a common piece in the structural patchwork of signalling proteins. *Trends Biochem. Sci* 18, 343–348.

Philpott, K. L., McCarthy, M. J., Klippel, A. & Rubin, L. L. (1997) Activated phosphatidylinositol 3-kinase and Akt kinase promote survival of superior cervical neurons. *J. Cell. Biol.* 139, 809–815.

Sheperd, P. R., Withers, D. J. & Siddle, K. (1998) Phosphoinositide 3-kinase: the key switch mechanism in insulin signalling. *Biochem J.* 333, 471–490.

Stephens, L., Anderson, K., Stokoe, D., Erdjumentbromage, H., Painter, G. F., Homes, A. B., Gaffney, P. R. J., Reese, C. B., McCormick, F., Tempst, P., Coadwell, J. & Hawkins, P. T. (1998) Protein kinase B kinases that mediate phosphatidylinositol 3,4,5-trisphosphate-dependent activation of protein kinase B. *Science,* 279, 710–714.

Staal, S. P. (1987) Molecular cloning of the akt oncogene and its human homologues AKT1 and AKT2: amplification of AKT1 in a primary human gastric adenocarcinoma. *Proc. Natl. Acad. Sci. USA* 89, 9267–9271.

Stokoe, D., Stephens, L. R., Copeland, T., Gaffney, P. R. J., Reese, C. B. & Painter, G. F. (1997) Dual role of phosphatidylinositol-3,4,5-triphosphate in the activation of protein kinase B. *Science* 277, 567–570.

Walker, K. S., Deak, M., Paterson, A., Hudson, K., Cohen, P. & Alessi, D. R. (1998) Activation of protein kinase β and γ isoforms by insulin in vivo and by 3-phosphoinositide-dependent protein kinase-1 in vitro: comparison with protein kinase B α. *Biochem. J.* 331, 299–308.

The invention claimed is:

1. An isolated nucleic acid molecule encoding human Akt-3 protein, comprising the amino acid sequence illustrated in SEQ ID No. 3.

2. The nucleic acid molecule according to claim 1 which is a DNA molecule.

3. The nucleic acid molecule according to claim 1 comprising the nucleotide sequence illustrated in SEQ ID No. 1.

4. The nucleic acid molecule according to claim 1 comprising the nucleotide sequence in SEQ ID No. 2.

5. An expression vector comprising the nucleic acid molecule according to claim 2.

6. The expression vector according to claim 5 comprising an inducible promoter.

7. The expression vector according to claim 5 comprising a sequence encoding a reporter molecule.

8. An isolated host cell, transformed or transfected with the expression vector according to claim 5.

9. An isolated transgenic cell comprising the nucleic acid molecule of claim 1, which expresses human Akt-3 protein as a transgene.

* * * * *

SEQUENCE LISTING

<160> NUMBER OF SEQ ID NOS: 16

<210> SEQ ID NO 1
<211> LENGTH: 1547
<212> TYPE: DNA
<213> ORGANISM: Homo sapiens

<400> SEQUENCE: 1

| | | | | | | |
|---|---|---|---|---|---|---|
| gggagtcatc | atgagcgatg | ttaccattgt | gaaagaaggt | tgggttcaga | agaggggaga | 60 |
| atatataaaa | aactggaggc | caagatactt | cctttttgaag | acagatggct | cattcatagg | 120 |
| atataaagag | aaacctcaag | atgtggattt | accttatccc | ctcaacaact | tttcagtggc | 180 |
| aaaatgccag | ttaatgaaaa | cagaacgacc | aaagccaaac | acatttataa | tcagatgtct | 240 |
| ccagtggact | actgttatag | agagaacatt | tcatgtagat | actccagagg | aaagggaaga | 300 |
| atggacagaa | gctatccagg | ctgtagcaga | cagactgcag | aggcaagaag | aggagagaat | 360 |
| gaattgtagt | ccaacttcac | aaattgataa | tataggagag | aagagatgg | atgcctctac | 420 |
| aacccatcat | aaaagaaaga | caatgaatga | ttttgactat | ttgaaactac | taggtaaagg | 480 |
| cactttttggg | aaagttatttt | tggttcgaga | gaaggcaagt | ggaaaatact | atgctatgaa | 540 |
| gattctgaaa | aaagaagtca | ttattgcaaa | ggatgaagtg | gcacacactc | taactgaaag | 600 |
| cagagtatta | aagaacacta | gacatccctt | tttaacatcc | ttgaaatatt | ccttccagac | 660 |
| aaaagaccgt | ttgtgttttg | tgatggaata | tgttaatggg | ggcgagctgt | ttttccattt | 720 |
| gtcgagagag | cgggtgttct | ctgaggaccg | cacacgtttc | tatggtgcag | aaattgtctc | 780 |
| tgccttggac | tatctacatt | ccggaaagat | tgtgtaccgt | gatctcaagt | tggagaatct | 840 |
| aatgctggac | aaagatggcc | acataaaaat | tacagatttt | ggactttgca | agaagggat | 900 |
| cacagatgca | gccaccatga | agacattctg | tggcactcca | gaatatctgg | caccagaggt | 960 |
| gttagaagat | aatgactatg | gccgagcagt | agactggtgg | ggcctagggg | ttgtcatgta | 1020 |
| tgaaatgatg | tgtgggaggt | taccttttcta | caaccaggac | catgagaaac | tttttgaatt | 1080 |
| aatattaatg | gaagacatta | aatttcctcg | aacactctct | tcagatgcaa | aatcattgct | 1140 |
| ttcagggctc | ttgataaagg | atccaaataa | acgccttggt | ggaggaccag | atgatgcaaa | 1200 |
| agaaattatg | agacacagtt | tcttctctgg | agtaaactgg | caagatgtat | atgataaaaa | 1260 |
| gcttgtacct | cctttttaaac | ctcaagtaac | atctgagaca | gatactagat | attttgatga | 1320 |
| agaatttaca | gctcagacta | ttacaataac | accacctgaa | aaatatgatg | aggatggtat | 1380 |
| ggactgcatg | gacaatgaga | ggcggccgca | tttccctcaa | ttttcctact | ctgcaagtgg | 1440 |
| acgagaataa | gtctctttca | ttctgctact | tcactgtcat | cttcaattta | ttactgaaaa | 1500 |
| tgattcctgg | acatcaccag | tcctagctct | tacacatagc | aggggca | | 1547 |

<210> SEQ ID NO 2
<211> LENGTH: 1437
<212> TYPE: DNA
<213> ORGANISM: Homo sapiens

<400> SEQUENCE: 2

| | | | | | | |
|---|---|---|---|---|---|---|
| atgagcgatg | ttaccattgt | gaaagaaggt | tgggttcaga | agaggggaga | atatataaaa | 60 |
| aactggaggc | caagatactt | cctttttgaag | acagatggct | cattcatagg | atataaagag | 120 |
| aaacctcaag | atgtggattt | accttatccc | ctcaacaact | tttcagtggc | aaaatgccag | 180 |
| ttaatgaaaa | cagaacgacc | aaagccaaac | acatttataa | tcagatgtct | ccagtggact | 240 |

```
actgttatag agagaacatt tcatgtagat actccagagg aaagggaaga atggacagaa    300
gctatccagg ctgtagcaga cagactgcag aggcaagaag aggagagaat gaattgtagt    360
ccaacttcac aaattgataa ataggagag gaagagatgg atgcctctac aacccatcat    420
aaaagaaaga caatgaatga ttttgactat ttgaaactac taggtaaagg cacttttggg    480
aaagttattt tggttcgaga gaaggcaagt ggaaaatact atgctatgaa gattctgaag    540
aaagaagtca ttattgcaaa ggatgaagtg gcacacactc taactgaaag cagagtatta    600
aagaacacta gacatcccTT tttaacatcc ttgaaatatt ccttccagac aaaagaccgt    660
ttgtgttttg tgatggaata tgttaatggg ggcgagctgt ttttccatTT gtcgagagag    720
cgggtgttct ctgaggaccg cacacgtttc tatggtgcag aaattgtctc tgccttggac    780
tatctacatt ccggaaagat tgtgtaccgt gatctcaagt tggagaatct aatgctggac    840
aaagatggcc acataaaaat tacagattTT ggactttgca agaagggat cacagatgca    900
gccaccatga agacattctg tggcactcca gaatatctgg caccagaggt gttagaagat    960
aatgactatg gccgagcagt agactggtgg ggcctagggg ttgtcatgta tgaaatgatg    1020
tgtgggaggt tacctttcta caaccaggac catgagaaac ttttTgaatt aatattaatg    1080
gaagacatta aatttcctcg aacactctct tcagatgcaa aatcattgct ttcagggctc    1140
ttgataaagg atccaaataa acgccttggt ggaggaccag atgatgcaaa agaaattatg    1200
agacacagtt tcttctctgg agtaaactgg caagatgtat atgataaaaa gcttgtacct    1260
ccttttaaac ctcaagtaac atctgagaca gatactagat attttgatga agaatttaca    1320
gctcagacta ttacaataac accacctgaa aaatatgatg aggatggtat ggactgcatg    1380
gacaatgaga ggcggccgca tttccctcaa ttttcctact ctgcaagtgg acgagaa      1437
```

<210> SEQ ID NO 3
<211> LENGTH: 479
<212> TYPE: PRT
<213> ORGANISM: Homo sapiens

<400> SEQUENCE: 3

```
Met Ser Asp Val Thr Ile Val Lys Glu Gly Trp Val Gln Lys Arg Gly
 1               5                  10                  15

Glu Tyr Ile Lys Asn Trp Arg Pro Arg Tyr Phe Leu Leu Lys Thr Asp
             20                  25                  30

Gly Ser Phe Ile Gly Tyr Lys Glu Lys Pro Gln Asp Val Asp Leu Pro
         35                  40                  45

Tyr Pro Leu Asn Asn Phe Ser Val Ala Lys Cys Gln Leu Met Lys Thr
     50                  55                  60

Glu Arg Pro Lys Pro Asn Thr Phe Ile Ile Arg Cys Leu Gln Trp Thr
 65                  70                  75                  80

Thr Val Ile Glu Arg Thr Phe His Val Asp Thr Pro Glu Glu Arg Glu
                 85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160
```

```
Lys Val Ile Leu Val Arg Glu Lys Ala Ser Gly Lys Tyr Tyr Ala Met
                165                 170                 175
Lys Ile Leu Lys Lys Glu Val Ile Ile Ala Lys Asp Glu Val Ala His
            180                 185                 190
Thr Leu Thr Glu Ser Arg Val Leu Lys Asn Thr Arg His Pro Phe Leu
        195                 200                 205
Thr Ser Leu Lys Tyr Ser Phe Gln Thr Lys Asp Arg Leu Cys Phe Val
    210                 215                 220
Met Glu Tyr Val Asn Gly Gly Glu Leu Phe Phe His Leu Ser Arg Glu
225                 230                 235                 240
Arg Val Phe Ser Glu Asp Arg Thr Arg Phe Tyr Gly Ala Glu Ile Val
                245                 250                 255
Ser Ala Leu Asp Tyr Leu His Ser Gly Lys Ile Val Tyr Arg Asp Leu
            260                 265                 270
Lys Leu Glu Asn Leu Met Leu Asp Lys Asp Gly His Ile Lys Ile Thr
        275                 280                 285
Asp Phe Gly Leu Cys Lys Glu Gly Ile Thr Asp Ala Ala Thr Met Lys
    290                 295                 300
Thr Phe Cys Gly Thr Pro Glu Tyr Leu Ala Pro Glu Val Leu Glu Asp
305                 310                 315                 320
Asn Asp Tyr Gly Arg Ala Val Asp Trp Trp Gly Leu Gly Val Val Met
                325                 330                 335
Tyr Glu Met Met Cys Gly Arg Leu Pro Phe Tyr Asn Gln Asp His Glu
            340                 345                 350
Lys Leu Phe Glu Leu Ile Leu Met Glu Asp Ile Lys Phe Pro Arg Thr
        355                 360                 365
Leu Ser Ser Asp Ala Lys Ser Leu Leu Ser Gly Leu Leu Ile Lys Asp
    370                 375                 380
Pro Asn Lys Arg Leu Gly Gly Pro Asp Asp Ala Lys Glu Ile Met
385                 390                 395                 400
Arg His Ser Phe Phe Ser Gly Val Asn Trp Gln Asp Val Tyr Asp Lys
                405                 410                 415
Lys Leu Val Pro Pro Phe Lys Pro Gln Val Thr Ser Glu Thr Asp Thr
            420                 425                 430
Arg Tyr Phe Asp Glu Glu Phe Thr Ala Gln Thr Ile Thr Ile Thr Pro
        435                 440                 445
Pro Glu Lys Tyr Asp Glu Asp Gly Met Asp Cys Met Asp Asn Glu Arg
    450                 455                 460
Arg Pro His Phe Pro Gln Phe Ser Tyr Ser Ala Ser Gly Arg Glu
465                 470                 475

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accatttctc caagttgggg gctcag                                      26

<210> SEQ ID NO 5
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 5
gggagtcatc atgagcgatg ttacc                                              25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cactccagaa tatctggcac cagagg                                             26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctatggccga gcagtagact ggtgg                                              25

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgcccctgct atgtgtaaga gctagg                                             26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagagctagg actggtgatg tccagg                                             26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgaaggtcgg agtcaacgga tttggt                                             26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 11
gggttgtaga ggcatccatc tcttcc                                          26

<210> SEQ ID NO 12
<211> LENGTH: 28
<212> TYPE: PRT
<213> ORGANISM: Homo sapiens

<400> SEQUENCE: 12

Tyr Asp Glu Asp Gly Met Asp Cys Met Asp Asn Glu Arg Arg Pro His
 1               5                  10                  15

Phe Pro Gln Phe Ser Tyr Ser Ala Ser Gly Arg Glu
             20                  25

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      (HA) tag

<400> SEQUENCE: 13

Tyr Pro Tyr Asp Val Pro Asp Tyr Ala
 1               5

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catgtgggcc atgaggtcca ccac                                            24

<210> SEQ ID NO 15
<211> LENGTH: 480
<212> TYPE: PRT
<213> ORGANISM: Homo sapiens

<400> SEQUENCE: 15

Met Ser Asp Val Ala Ile Val Lys Glu Gly Trp Leu His Lys Arg Gly
 1               5                  10                  15

Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
         35                  40                  45

Glu Ala Pro Leu Asn Asn Phe Ser Val Ala Gln Cys Gln Leu Met Lys
     50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125
```

Ser Gly Ala Glu Glu Met Glu Val Ser Leu Ala Lys Pro Lys His Arg
130             135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
                180                 185                 190

Ala His Thr Leu Thr Glu Asn Arg Val Leu Gln Asn Ser Arg His Pro
            195                 200                 205

Phe Leu Thr Ala Leu Lys Tyr Ser Phe Gln Thr His Asp Arg Leu Cys
210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
                340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
435                 440                 445

Ile Thr Pro Pro Asp Gln Asp Asp Ser Met Glu Cys Val Asp Ser Glu
            450                 455                 460

Arg Arg Pro His Phe Pro Gln Phe Ser Tyr Ser Ala Ser Gly Thr Ala
465                 470                 475                 480

<210> SEQ ID NO 16
<211> LENGTH: 481
<212> TYPE: PRT
<213> ORGANISM: Homo sapiens

<400> SEQUENCE: 16

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
                20                  25                  30

```
Gly Ser Phe Ile Gly Tyr Lys Glu Arg Pro Glu Ala Pro Asp Gln Thr
            35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
                100                 105                 110

Arg Ala Pro Gly Glu Asp Pro Met Asp Tyr Lys Cys Gly Ser Pro Ser
            115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
                180                 185                 190

Glu Val Ala His Thr Val Thr Glu Ser Arg Val Leu Gln Asn Thr Arg
            195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
                260                 265                 270

Tyr Arg Asp Ile Lys Leu Glu Asn Leu Met Leu Asp Lys Asp Gly His
            275                 280                 285

Ile Lys Ile Thr Asp Phe Gly Leu Cys Lys Glu Gly Ile Ser Asp Gly
    290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
                340                 345                 350

Gln Asp His Glu Arg Leu Phe Glu Leu Ile Leu Met Glu Glu Ile Arg
            355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
    435                 440                 445
```

```
-continued

Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

Glu
```